United States Patent
Hirai

(10) Patent No.: US 9,435,871 B2
(45) Date of Patent: Sep. 6, 2016

(54) MAGNETIC RESONANCE IMAGING APPARATUS AND FLUID-ENHANCED IMAGE ACQUISITION METHOD

(75) Inventor: Kosuke Hirai, Tokyo (JP)

(73) Assignee: HITACHI MEDICAL CORPORATION, Tokyo (JP)

(*) Notice: Subject to any disclaimer, the term of this patent is extended or adjusted under 35 U.S.C. 154(b) by 533 days.

(21) Appl. No.: 13/978,930

(22) PCT Filed: Jan. 11, 2012

(86) PCT No.: PCT/JP2012/050295
§ 371 (c)(1),
(2), (4) Date: Jul. 10, 2013

(87) PCT Pub. No.: WO2012/098955
PCT Pub. Date: Jul. 26, 2012

(65) Prior Publication Data
US 2013/0293231 A1    Nov. 7, 2013

(30) Foreign Application Priority Data

Jan. 17, 2011 (JP) ................................ 2011-006551

(51) Int. Cl.
*G01V 3/00* (2006.01)
*G01R 33/48* (2006.01)
*A61B 5/055* (2006.01)
*G01R 33/563* (2006.01)
*G01R 33/561* (2006.01)
(Continued)

(52) U.S. Cl.
CPC ........... *G01R 33/4828* (2013.01); *A61B 5/055* (2013.01); *G01R 33/5635* (2013.01); *G01R 33/4836* (2013.01); *G01R 33/5602* (2013.01); *G01R 33/5613* (2013.01)

(58) Field of Classification Search
USPC ........................................................ 324/309
See application file for complete search history.

(56) References Cited

U.S. PATENT DOCUMENTS

| 5,270,653 A | 12/1993 | Pauly | |
| 8,515,526 B2* | 8/2013 | Miyazaki | ............... A61B 5/055 600/410 |
| 2004/0162483 A1* | 8/2004 | Kimura | ............ G01R 33/56308 600/419 |

(Continued)

FOREIGN PATENT DOCUMENTS

| JP | 7-308302 | 11/1995 |
| JP | 2001-252263 | 9/2001 |

(Continued)

OTHER PUBLICATIONS

International Search Report in PCT/JP2012/050295.

(Continued)

*Primary Examiner* — Rodney Fuller
(74) *Attorney, Agent, or Firm* — Cooper & Dunham LLP

(57) ABSTRACT

In order to acquire an image with enhanced contrast between a fluid portion and a stationary portion without extending the imaging time even when an IR pulse is used as an RF pre-pulse, the RF pre-pulse is applied to a region upstream of an imaging region so as to excite longitudinal magnetization of the fluid portion in a negative direction, an echo signal is measured from the imaging region, and an image with enhanced contrast of the fluid portion with respect to the stationary portion is acquired on the basis of phase information of an image reconstructed by using the echo signal.

15 Claims, 18 Drawing Sheets

(51) Int. Cl.
   *G01R 33/483* (2006.01)
   *G01R 33/56* (2006.01)

(56) References Cited

U.S. PATENT DOCUMENTS

| | | | |
|---|---|---|---|
| 2009/0171186 A1 | 7/2009 | Takei | |
| 2010/0022869 A1 | 1/2010 | Kimura | |
| 2011/0031971 A1* | 2/2011 | Deimling | G01R 33/5614 324/309 |
| 2011/0071382 A1* | 3/2011 | Miyazaki | A61B 5/0037 600/413 |
| 2013/0266199 A1* | 10/2013 | Nishihara | A61B 5/055 382/131 |

FOREIGN PATENT DOCUMENTS

| | | |
|---|---|---|
| JP | 2001-299724 | 10/2001 |
| JP | 2004-261619 | 9/2004 |
| JP | 2009-160122 | 7/2009 |
| JP | 2010-46473 | 3/2010 |
| JP | 2011-254905 | 12/2011 |

OTHER PUBLICATIONS

Translation of Feb. 9, 2015 Chinese official action in corresponding Chinese Patent Application No. 201280005598.2.

* cited by examiner

FIG. 4
(a) PRIMARY REPHASE
1:-2:1
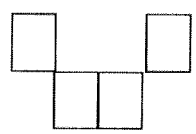
(b) SECONDARY REPHASE
1:-3:3:-1
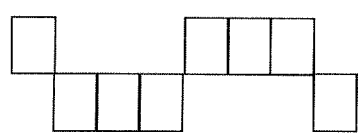

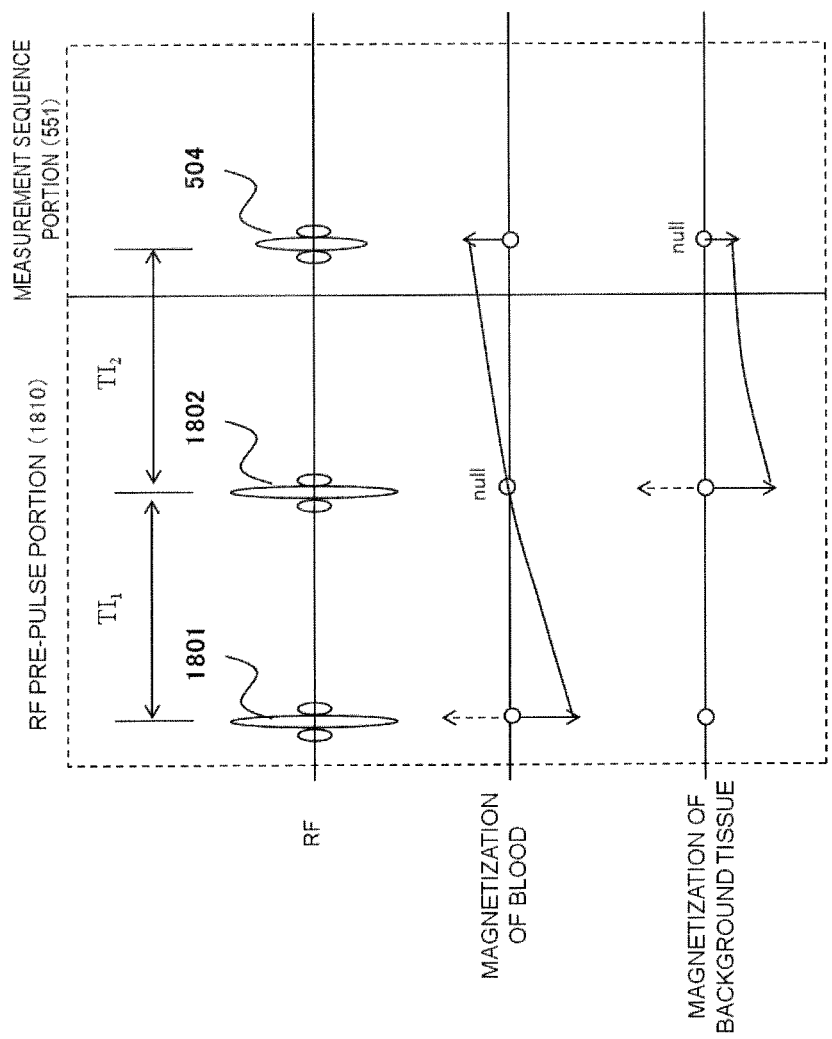

MAGNETIC RESONANCE IMAGING APPARATUS AND FLUID-ENHANCED IMAGE ACQUISITION METHOD

FIELD OF THE INVENTION

The present invention relates to a technique for obtaining an image with enhanced contrast between a desired tissue and other tissue at the time of imaging a cross-sectional image using a nuclear magnetic resonance (hereinafter referred to as NMR) phenomenon (hereinafter referred to as MRI).

DESCRIPTION OF RELATED ART

An MRI apparatus for obtaining cross-sectional images using NMR phenomenon measures NMR signals produced by nuclear spin which constitutes an object, a human body in particular, and performs 2-dimensional or 3-dimensional imaging of shapes or functions of the head region, abdominal region, extremities, and so on. In the imaging, the NMR signals are provided with different phase encodes depending on a gradient magnetic field, to be frequency-encoded and measured as time-series data. The measured NMR signals are 2-dimensionally or 3-dimensionally Fourier-transformed to be constructed as an image.

One of the commonly known imaging methods using the above-described MRI apparatus for obtaining images by setting a different contrast on fluid that flows in a body such as blood or spinal fluid from the other tissue (stationary tissue, etc.) the method which uses an IR (Inversion Recovery) pulse as a preceding pulse (RF pre-pulse) (for example, Patent Document 1). In concrete terms, an IR pulse is irradiated to a first region which is a region in the upstream side where the fluid passes, the longitudinal magnetization of the fluid in the first region is flipped (excited) by 180 degrees, and an echo signal is measured in a second region downstream into which the IR-pulsed fluid had flown at the time that the longitudinal magnetization of the fluid which is flipped by 180 degrees recovered by T1 relaxation and reached null condition. The operation to flip the longitudinal magnetization of fluid in the upstream side at a predetermined angle is referred to as labeling. This operation suppresses only the echo signal from the fluid, and enhances the contrast by generating the difference in pixel values (absolute values) between the fluid and the other tissue (stationary portion) in an image (absolute value image) in the second region.

PRIOR ART DOCUMENTS

Patent Documents

Patent Document 1: JP-2009-10113

Non-Patent Documents

Non-patent Document 1: Lauenstein T C et al; Evaluation of optimized inversion-recovery fat-suppression techniques for T2-weighted abdominal MR Imaging: J Magn Reson Imaging 2008:27:1418-1454

Non-patent Document 2: J. Pauly, D. Nishimura; A K-Space Analysis of Smaii-Tip-angle Excitation: J. Magn. Reson., 81, 43-56 (1989)

SUMMARY OF INVENTION

Technical Problem

However, a predetermined standby time (TI) is required in order to make the longitudinal magnetization of fluid be in null condition before the measurement of echo signals using an IR pulse as an RF pulse, and the difficulty of reducing imaging time still remains as a problem. Also in the images obtained using an IR pulse, insufficiency of contrast enhancement between fluid and the other tissue still remains as a problem.

Considering the above-described problem, the objective of the present invention is to provide the MRI apparatus and method for obtaining fluid enhanced images capable of obtaining images in which the contrast between a fluid portion and a stationary portion is enhanced without extending the imaging time even when using an IR pulse as an RF pre-pulse.

BRIEF SUMMARY OF THE INVENTION

In order to achieve the above-described objective, the present invention excites the longitudinal magnetization of a fluid portion in a negative direction by applying an RF pre-pulse to a region upstream-region from the imaging region, measures the echo signals from the imaging region, and obtains an image with enhanced contrast between the fluid portion and the stationary portion using phase information of an image reconstructed using the echo signals.

In concrete terms, the MRI apparatus of the present invention comprises:

a measurement control unit configured to control the measurement of echo signals from an imaging region of an object to be examined including a fluid portion, on the basis of a predetermined pulse sequence; and an arithmetic processing unit configured to obtain an image with enhanced contrast between a fluid portion and a stationary portion using the echo signals, wherein:

the pulse sequence includes an RF pre-pulse portion which comprises an RF pre-pulse for labeling a fluid portion by exciting the longitudinal magnetization of the fluid portion in a negative direction and a measurement sequence portion for measuring echo signals from the imaging region into which the labeled fluid portion had flown; and the arithmetic processing unit obtains a fluid-enhanced image with enhanced contrast between a fluid portion and a stationary portion on the basis of positional information of the image.

Also, the fluid enhanced image acquisition method of the present invention includes:

a measurement step of controlling the measurement of echo signals from an imaging region of an object to be examined including a fluid portion on the basis of a predetermined pulse sequence; and an arithmetic processing step of acquiring an image with enhanced contrast between a fluid portion and a stationary portion using the echo signals, wherein:

the pulse sequence includes an RF pre-pulse portion comprising an RF pre-pulse for labeling a fluid portion by exciting the longitudinal magnetization of the fluid portion in a negative direction, and a measurement sequence portion for measuring echo signals from an imaging region into which the labeled fluid portion is flow;

the measurement step applies an RF pre-pulse to the region upstream from the imaging region to execute the measurement sequence portion before the longitudinal magnetization of the fluid portion is recovered, and the arithmetic processing step acquires an image with enhanced contrast between a fluid portion and a stationary portion on the basis of the phase information of the image.

Effect of the Invention

In accordance with the MRI apparatus and the fluid enhanced image acquisition method, it is possible to obtain images in which the contrast between a fluid portion and a stationary portion is enhanced without extending the imaging time even when using an IR pulse as an RF pre-pulse.

BRIEF DESCRIPTION OF THE DRAWINGS

FIG. 2 shows a case in which standby time (T1) is set which is the time spent for the longitudinal magnetization flipped 180 degrees by an IR pulse to recover by T1 and acquire the null condition to be in the positive direction, wherein FIG. 2(a) shows the timing that an RF pulse (RF) is applied and the timing that an echo signal (signal) is generated. It also indicates the behavior of magnetization, corresponding to the respective timings of the pulse sequence, in a fluid portion which is labeled in a first region and in a stationary portion in a second region. FIG. 2(b) is a phantom example including a fluid portion to which water low in a U-shaped tube in a stationary portion from the left side toward the right side. FIG. 2(c) is an example of an absolute value image and a phase image obtained in the case that the phantom shown in (b) is imaged using the pulse sequence in shown in FIG. 2(a).

FIG. 3(a) shows the timing that an RF pulse (RF) is applied and the timing that an echo signal (signal) is generated, and also indicates the behavior of magnetization in a fluid portion in a first region and in a stationary portion in a second region to match the respective timings of the pulse sequence. FIG. 3(b) is an example of an absolute value image and a phase image to be obtained in the case that a phantom shown in FIG. 2(b) is imaged using the pulse sequence shown in FIG. 3(a).

FIG. 4 is an example of a rephase gradient magnetic field pulse in the commonly known GMN (Gradient Moment Nulling) method. FIG. 4(a) is an example of a primary rephase gradient magnetic field pulse waveform, and FIG. 4(b) is an example secondary rephase gradient magnetic field pulse waveform.

FIG. 18 shows the timing for applying the respective IR pulses in an RF pre-pulse portion and the behavior of the longitudinal magnetization in Embodiment 4.

DETAILED DESCRIPTION OF THE INVENTION

Figure 1:
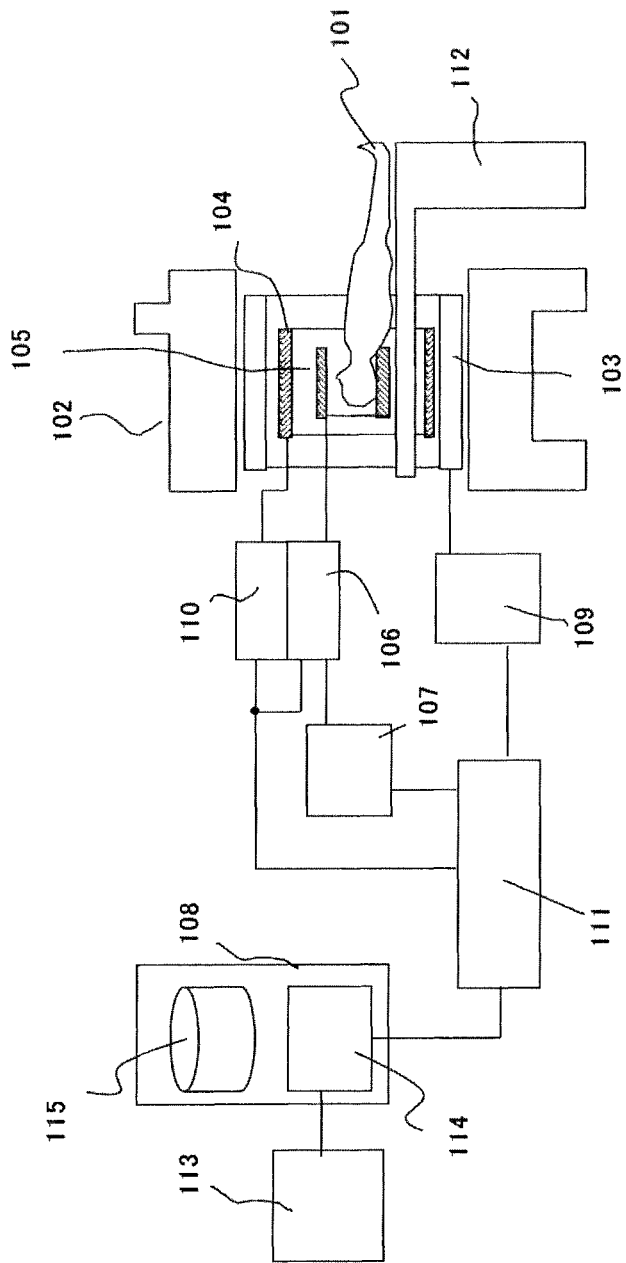
FIG. 1 is a block diagram showing the general configuration of an embodiment in the MRI apparatus related to the present invention.

The preferable embodiments of the MRI apparatus in the present invention will be described in detail below referring to the attached diagrams. In all diagrams for explaining the embodiments of the invention, the same function parts are represented by the same reference numerals, and the duplicative description thereof is omitted.

First, the MRI apparatus related to the present invention will be described referring to FIG. 1. FIG. 1 is a block diagram showing the general configuration of an embodiment of the MRI apparatus related to the present invention.

The MRI apparatus is for obtaining a tomographic image of an object 101 using NMR phenomenon, comprising a static magnetic field generating magnet 102, a gradient magnetic field coil 103 and a gradient magnetic field source 109, an RF transmission coil 104 and an RF transmission unit 110, an RF reception coil 105 and a signal detection unit 106, a signal processing unit 107, a measurement control unit 111, an overall control unit 108, a display/operation unit 113, and a bed 112 for carrying a top panel on which the object 101 is placed in and out of the inside of the static magnetic field generating magnet 102, as shown in FIG. 1.

The static magnetic field generating magnet 102 is for generating a uniform static magnetic field respectively in the direction orthogonal to the body axis f the object 101 if the vertical magnetic field method is applied and in the body axis direction if the horizontal magnetic field method is applied, and a static magnetic field generating source of the permanent magnetic method, normal conductive method or the superconductive method is to be placed around the object 101.

The gradient magnetic field coil 103 is wound in 3-axes direction of X, Y and Z which is the real-space coordinate system (static coordinate system) of the MRI apparatus, and the respective gradient magnetic field coils are connected to the gradient magnetic field source 109 for driving them and supplied with current. In concrete terms, the gradient magnetic field source 109 of the respective gradient magnetic field coils is activated according to the command from the measurement control unit 111 to be described later, and supplies the current to the respective gradient magnetic field coils. In this manner, gradient magnetic fields Gx, Gy and Go are generated in the 3-axes direction of X, Y and Z.

At the time of imaging a 2-dimensional slice plane, a slice plane with respect to the object 101 is set by applying slice gradient magnetic field pulse (Gs) in the direction orthogonal to the slice plane (imaging cross-section), then phase encode gradient magnetic field pulse (Gp) and a readout gradient magnetic field pulse (Gf) are applied to the remaining two directions that are orthogonal to the slice plane and to each other, and the positional information in the respective directions is encoded to an NMR signal (echo signal).

The RF transmission coil 104 is for irradiating an RF pulse to the object 101, and is connected to an RF transmission unit 110 to be supplied with a high-frequency pulse current. In this manner, the NMR phenomenon is excited to the nuclear spin that forms the biological tissue of the object 101. In concrete terms, the RF transmission unit 110 is activated according to the command from the measurement control unit 111 to be described later, a high-frequency pulse is amplitude-modulated, amplified, and supplied to the RF transmission coil 104 which is placed in the vicinity of the object 101, then an RF pulse is irradiated to the object 101.

The RF reception coil 105 is for receiving the echo signal discharged by NMR phenomenon of the spin that forms the biological tissue of the objet 101, which is connected to the signal detection unit 106, and the received echo signal is transmitted to the signal detection unit 106.

The signal detection unit 106 detects the echo signal received by the RF reception coil 105. In concrete terms, in accordance with the command from the measurement control unit 111 to be described later, the signal detection unit 106 amplifies the received echo signal, divides the signal into two channels of signals that are orthogonal to each other by quadrature phase detection, performs predetermined numbers (for example, 128, 256, 512, etc.) of sampling on each divided signals, executes A/D conversion on the respective sampling signals into digital amount, and transmits the converted amount to the signal processing unit 107 to be described later. Accordingly, the echo signals are acquired as time-series digital data (hereinafter referred to as echo data) formed by predetermined numbers of sampling data.

The signal processing unit 107 executes various processing on the echo data, and transmits the processed echo data to the measurement control unit 111.

The measurement control unit 111 transmits various commands for collecting echo data necessary for reconstruction of a tomographic image of the object 101 mainly to the gradient magnetic field source 109, the RF transmission unit 110 and the signal detection unit 106 and controls the respective components. In concrete terms, the measurement control unit 111 which is under control of the overall control unit 108 to be described later, by controlling the gradient magnetic field source 109, the RF transmission unit 110 and the signal detection unit 106 on the basis of a predetermined pulse sequence, repeatedly executes the irradiation of an RF pulse and application of a gradient magnetic field pulse to the object 101 and detection of an echo signal from the object 101, and controls the collection of echo data necessary for reconstruction of images in an imaging region of the object 101. At the time of repetitive application of gradient magnetic field pulses, the application amount of a phase encode gradient magnetic field is to be varied for 2-dimensional imaging, and the application amount of a slice encode gradient magnetic field is also to be varied for 3-dimensional imaging. The number of phase encoding steps to be selected per a piece of image is generally 128, 256, 512, etc., and the number of slice encoding steps is generally 16, 32, 64, etc. In this manner, the echo data from the signal processing unit 107 is output to the overall control unit 108.

The overall control unit 108 is for controlling the measurement control unit 111, various data processing and display and storage, etc. of the processing result, and comprises the arithmetic processing unit 114 which contains a CPU and a memory therein and a storage unit 115 such as an optical disk and a magnetic disk. In concrete terms, the overall control unit 118 controls the measurement control unit 111 to carry out the collection of echo data, and when the echo data from the measurement control unit 111 is input, the arithmetic processing unit 119 makes the echo data stored in the region equivalent to the k-space in the memory on the basis of the encode information applied to the encode data. Hereinafter, the description on the placement of echo data in the k-space means that the echo data is stored in the region equivalent to the k-space in the memory.

Also, an echo data group stored in the region equivalent to the k-space in the memory is referred to as k-space data. The arithmetic processing unit 114 performs processing on the k-space data, such as signal processing or image reconstruction by Fourier conversion, and displays an image of the object 101 which is the result of the processing on the display/operation unit 113 to be described later and stores the image in the storage unit 115.

The display/operation unit 113 is formed by a display unit configured to display a reconstructed image of the object 101 and an operation unit formed by devices such as a trackball or a mouse and a keyboard configured to input various control information of the MRI apparatus or the control information on the processing to be executed in the overall control unit 108. The operation unit is placed in the vicinity of the display unit, for an operator to interactively control various processing of the MRI apparatus via the operation unit while observing the display unit.

Currently, an imaging target nuclide of an MRI apparatus widely used in clinical practice is hydrogen nucleus (proton) which is a main component of an object. By imaging the information related to the spatial distribution of proton density or information related the spatial distribution of relaxation time in the excitation condition, the shape or function of a human body part such a head region, abdominal region or extremities is 2-dimensionally or 3-dimensionally imaged.

(Description on the Magnetization and its Phase that are Related to the Present Invention)

Next, the principle of setting the phase difference to the transverse magnetizations of different tissues using an IR pulse as an RF pre-pulse will be described, which is the basis for the present invention. In the present invention, all RF pulses for providing an arbitrary T1 recovery time after flipping the longitudinal magnetization at an arbitrary flip angle will be referred to as an IR pulse. In this regard, however, the RF pre-pulse in the present invention is not limited to an IR pulse, and all RF pulses capable of flipping (exciting) the longitudinal magnetization at a desired angle can be used.

Also in the following description, the direction of the longitudinal magnetization before being flipped (i.e. excited) is set as a positive direction (static magnetic field direction), and the opposite direction is set as a negative direction (opposite direction from the static magnetic field direction). In this direction setting, the longitudinal magnetization before being flipped is in the maximum condition facing in the positive direction, and the magnetization faces in a negative direction right after being flipped to an angle larger than 90 degrees. Then the direction of the transverse magnetization generated when the longitudinal magnetization is flipped becomes perpendicular to the direction of the longitudinal magnetization.

As previously described, the conventional technique performs labeling on the upstream of fluid and measures the echo signals at the point, when the longitudinal magnetization of the fluid recovers to null condition for generating the intensity difference in the echo signals between the fluid and the other tissue (stationary portion), then reflects the intensity difference of the echo signals on an image to enhance the contrast between the fluid and the other stationary portion.

On the other hand, the present invention generates the phase difference of the transverse magnetization between fluid and the other tissue using an RF pre-pulse, so as to enhance the contrast between the fluid and the other tissue using the generated phase difference. Also, the contrast between fluid and the other tissue may further be enhanced by first generating the intensity difference in the echo signals between the fluid and the other tissue using the conventional technique, then further generating the phase difference using the present invention.

In this regard, the present invention measures echo signals from an object using the pulse sequence formed by an RF pre-pulse portion comprising an RF pre-pulse that flips (excites) the longitudinal magnetization in a first region upstream in a negative direction and a measurement sequence portion that measures the echo signals in a second region downstream before the longitudinal magnetization excited by the RF pre-pulse recovers to null (zero) or above. The RF pre-pulse needs to flip the longitudinal magnetization larger than 90 degrees and smaller than 270 degrees for exciting the longitudinal magnetization in a negative direction, thus it is to be set as an IR pulse for exciting the longitudinal magnetization at $\alpha-(90<\alpha<270)$ degrees. On the other hand, a commonly known pulse sequence may be used for the measurement sequence portion. By setting the flip angle of the RF pulse for generating the transverse magnetization in the measurement sequence portion as $\beta(0<\beta\leq90)$-degrees, flip angle $\alpha$-degrees of the IR pulse in the RF pre-pulse portion and flip angle $\beta$-degrees in the RF pulse for generating the transverse magnetization in the measurement sequence portion are determined, preferably as $\alpha=180$ and $\beta=90$.

Figure 2:
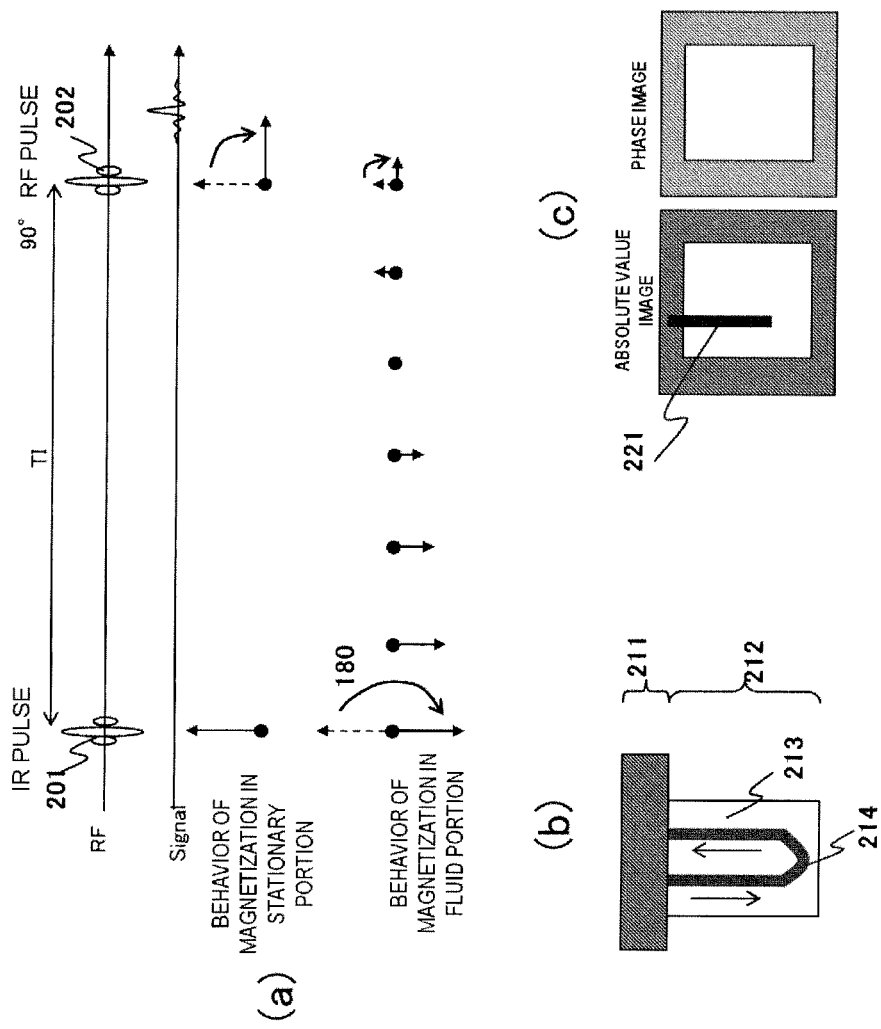
Figure 3:
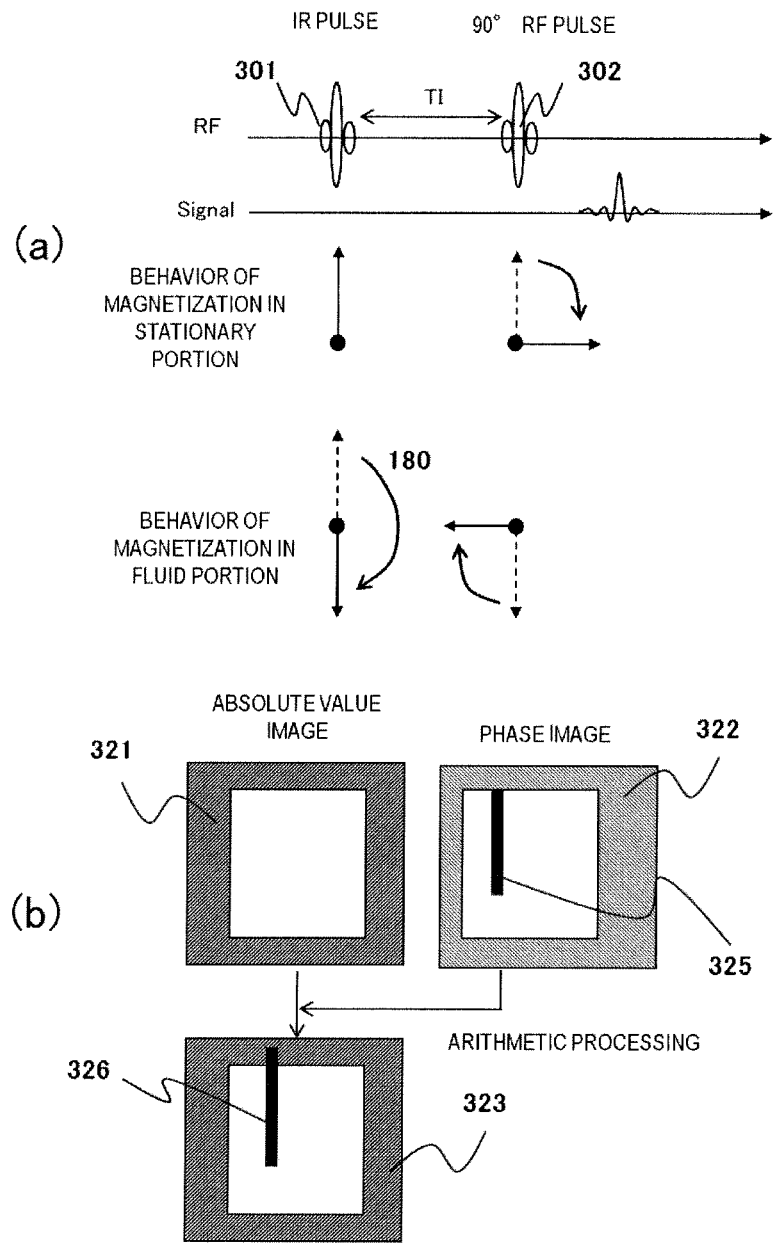
FIG. 3 shows a case that an echo signal is measured before the longitudinal magnetization which is flipped 180 degrees by an IR pulse is recovered by T1 to be above null (zero) condition by reducing the standby time (TI).

First, the fact that the phases of the transverse magnetization can be differentiated by e (i.e. differentiate polar characters of the phases) by the length of standby time (TI) from the application of an IR pulse in an RF pre-pulse portion to the transverse magnetization generating RF pulse in the measurement sequence portion (for example, 90-degrees of flip angle), referring to FIGS. 2 and 3.

A case that the contrast is enhanced by extending standby time (TI) will be described for comparison referring to FIG. 2. FIG. 2 shows a case which a long time that the longitudinal magnetization being flipped by 180 degrees by an IR pulse recovers by T1 to be in the positive direction condition by acquiring null (zero) condition is set as standby time (TI).

FIG. 2(a) indicates the timing for applying an Pt pulse (RF) and the timing that an echo signal is generated, and also indicates the behavior of magnetization in a fluid portion which is labeled in a first region and in a stationary region in a second region in accordance with the respective timings of the pulse sequence and in a stationary portion in a second region.

Since an IR pulse 201 is applied to the first region in the upstream side, the longitudinal magnetization of fluid exists in the first region is flipped by 180 degrees and becomes the maximum condition in a negative direction. That is, the longitudinal magnetization of fluid is labeled by the IR pulse 201. On the other hand, the IR pulse 201 is not applied to the stationary portion in the second region of the downstream side which is different from the first region, the longitudinal magnetization still maintains the maximum condition in the positive direction.

The fluid which is labeled with time moves from the first region toward the second region according to the flow velocity, and the longitudinal magnetization recovers by T1 in an exponential manner from the maximum state of negative direction toward the positive direction state. Then after passing of a certain period of time from the application of the RF pulse 201, the longitudinal magnetization of the fluid becomes null condition. After passing of further standby time (TI) from the application of the RF pulse 201, the fluid moves it position into the second region and the longitudinal magnetization becomes the condition of the positive direction, but this condition is smaller than the maximum condition in the positive direction. At this point, when an RF pulse 202 of 90-degrees for generating the transverse magnetization in the measurement sequence portion is applied to the second region, the fluid which is labeled in the first region and moved to the second region is flipped by 90-degrees again in the condition that the longitudinal magnetization in the positive direction remains small and becomes a small transverse magnetization condition. On the other hand, the longitudinal magnetization in the stationary portion in the second region is flipped by 90-degrees from the maximum condition in the positive direction, and reaches the maximum transverse magnetization condition. As a result, the transverse magnetization is larger in the stationary portion than in the fluid portion, but the transverse magnetization right after the excitation faces toward the same direction, thus the phases of the transverse magnetization becomes the same.

Therefore, in the echo signals measured in the measurement sequence portion in such transverse magnetization condition and the reconstructed image obtained from the echo signals, the absolute value becomes larger in the stationary portion than in the fluid portion, but the phases becomes the same in the stationary portion and the fluid portion. In other words, in the case of standby time (TI) which is long enough for the longitudinal magnetization of the fluid that is flipped by an IR pulse to be in the negative condition can recover to the positive condition, the difference of the absolute values is generated between the stationary portion and the fluid portion regarding the pixel values in the reconstructed image, but the difference of the phases is not generated. Accordingly, the contrast between the stationary portion and the fluid portion must be created only by the magnitude of the absolute values, which may be insufficient. In addition, the standby time (TI) having the maximum contrast between the stationary portion and the fluid portion by only the signal intensity is the time up until the longitudinal magnetization of the fluid portion which is flipped by 180 degrees and labeled becomes the null condition.

FIG. 2(c) is an example of an absolute value image and a phase image obtained in the case that a phantom shown in FIG. 2(b) is imaged using the pulse sequence shown in FIG.

2(*a*). The phantom shown in FIG. 2(*b*) comprises a fluid portion 214 in which water flows in a U-shaped tube in the stationary portion 213 from the left side toward the right side, wherein an IR pulse 201 is irradiated to a first region 211 which is the upstream part and an RF pulse 202 is irradiated to a second region 212 which is the downstream part. While the signal intensity of the left side region 221 of the U-shaped section is attenuated in the absolute value image since the fluid which is labeled by the IR pulse 201 in the first region 211 moves to the left side region of the U-shape section in the second region 212, the signal intensity becomes the same as the stationary portion 213 in the sequence U-shaped section region since the longitudinal magnetization of the fluid portion recovers by T1 to the maximum condition in the positive direction. Meanwhile, the phases of the transverse magnetization in the stationary portion 213 and the fluid portion 214 become the same, thus the phases of the stationary portion 213 and the fluid portion 214 become similar in the phase image.

On the other hand, the case in which the contrast is enhanced by reducing the standby time (TI) will be described referring to FIG. 3. FIG. 3 shows the case that the standby time (T1) is shortened and the echo signal is measured before the longitudinal magnetization which is flipped 180 degrees by an IR pulse recovers by T1 to null condition or above. The short standby time (TI) here means the time which is short enough that the longitudinal magnetization flipped by 90 degrees or more by the RF pre-pulse maintains a negative direction state without being recovered by T1 to null condition. More specifically, it is the standby time (TI) between an IR pulse for exciting the longitudinal magnetization of a fluid portion in the RF pre-pulse portion and labeling the fluid portion and a transverse magnetization generating RF pulse in a measurement sequence portion, so that the longitudinal magnetization of the fluid portion labeled by the IR pulse maintains a negative direction state.

FIG. 3(*a*) indicates the application timing of an RF pulse (RF) and the generation timing of the echo signal (signal) as in FIG. 2(*a*), and respectively indicates the behavior of magnetization of a fluid portion in a first region and a stationary portion in a second region based on each timing of the pulse sequence.

An IR pulse 301 is applied to the first region in the upstream side, thus the longitudinal magnetization of the fluid in the first region is flipped by 180 degrees to be in the maximum negative direction state. In other words, the longitudinal magnetization of the fluid is labeled by the IR pulse 301. On the other hand, the IR pulse 301 is not applied to the stationary portion in the second region which is different from the first region, thus the longitudinal direction therein maintains the maximum positive direction state without change.

Then the fluid portion labeled with time is transferred from the first region toward the second region in accordance with the flow velocity, and the longitudinal magnetization recovers by T1 from the maximum negative direction state in an exponential manner. Then after a short standby time (TI) in which the longitudinal magnetization of the fluid portion maintains the negative direction state without being recovered to null state or above and the fluid labeled in the first region is spread into the second region, an RF pulse 302 of 90 degrees for generating the transverse magnetization in the measurement sequence portion is applied to the second region.

As a result, the longitudinal magnetization of the stationary portion in the second region is flipped by 90 degrees from the maximum positive direction state to be in the maximum transverse state in the positive direction (here, the transverse magnetization direction of the stationary portion is referred to as the positive direction). On the other hand, the fluid portion which is labeled in the first region and transferred to the second region is flipped by 90 degrees again in the state that the longitudinal magnetization thereof remains largely in a negative direction, to be in the transverse magnetization state largely in a negative direction. In other words, while the magnitude of the transverse magnetization is not so different between the stationary portion and the fluid portion right after the 90-degrees RF pulse 302 is applied after the short standby time (TI), the phases of the transverse magnetization are different by $\pi$ (or, the polar characters of the phases are different) since the directions of the transverse magnetization faces the opposite direction from each other. Therefore, in the echo signals acquired from such transverse magnetization state or the reconstructed image obtained from such echo signals, the absolute values are not much different between the stationary portion and the fluid portion, but the phases are different by $\pi$ (or, the phase polar characters are different).

FIG. 3(*b*) is an example of the absolute value image and the phase image obtained in the case that a phantom shown in FIG. 2(*b*) is imaged using the pulse sequence shown in FIG. 3(*a*). The IR pulse 301 is irradiated to the first region 211 in the upstream part, and the RF pulse 302 is irradiated to the second region 212 in the downstream part. Though the fluid labeled by the IR pulse 301 in the first region 211 is transferred to the left-side part of the U-shaped section in the second region 212, the signal intensity difference between the stationary portion 213 and the fluid portion 214 is small in the absolute value image 321 including the left-side part of the U-shaped section since the standby time (TI) is short. On the other hand, since the phase of the transverse magnetization in the stationary portion 213 and the phase of the transverse magnetization in the fluid labeled by the IR pulse 301 in the first region 211 become the opposite phases (i.e., different by $\pi$), a great difference (i.e., a difference by $\pi$) is generated between the phase in the stationary portion 213 and the phase in a left-side region 325 of the U-shaped section in the fluid portion 214 in a phase image 322.

With that, by performing weighting calculation process on the respective pixel values in the absolute value image 321 based on the pixel values (i.e., phase values) corresponding to the phase image 322, it is possible to obtain an image 323, after performing the calculation, in which the contrast of a left-side region 326 of the U-shaped section into which the fluid labeled by the IR pulse 301 in the first region 211 is enhanced compared to the other stationary portion and the fluid portion.

Accordingly, the present invention obtains contrast-enhanced image, by performing the contrast enhancement process, on an image reconstructed using the echo signal that is measured by shortening the standby time (TI) after the fluid portion is labeled by an IR pulse, which enhances a labeled fluid portion with respect to the other stationary portion on the basis of the phase information of the image. In concrete terms, the weighting process is performed on the absolute value image having the absolute values of a complex using the phase difference between the fluid portion labeled in the reconstructed complex image of the object and the other stationary portion. In this manner, the imaging time is reduced compared to the case of contrast enhancement that the standby time (TI) is prolonged and only the absolute values of the pixels are used, and the contrast between the labeled fluid portion and the other stationary portion is further enhanced.

(For removal of phase errors due to other factors)

In general, since phase error which are generated by imaging other than the π phase difference (opposite phase polarity) given by a short standby time (TI) after the RF pre-pulse are mixed in the complex image, it is necessary to remove the phase errors.

The phase errors include a phase error which is accumulated during the measurement of the echo signal for an image due to resonance frequency shift such as static magnetic field ununiformity or chemical shift, a phase error due to incompleteness of hardware such as delay of a gradient magnetic field application timing with respect to A/D, and a phase error due to the motion of the object.

The phase error which is temporally accumulated due to the resonance frequency shift is negligible. It is generally known that the phase error is cancelled in a spin echo-based sequence which uses a 180° re-converging RF pulse between the excitation by the 90° RF pulse and the echo time TE, thus the phase error which is temporally accumulated is negligible. Meanwhile, in a gradient echo-based sequence, since there is no 180° re-converging RF pulse, the phase error which is temporally accumulated is not negligible.

For this reason, a phase image (reference phase image) is imaged by preliminary measurement (Pre-Scan) in advance when the RF pre-pulse is not applied, and a differential process between the phase image obtained by using the RF pre-pulse and the reference phase image is performed for obtaining a phase difference image, thereby removing the phase error which is temporally accumulated. The reference phase image which is obtained by pre-scan also includes the phase error due to incompleteness of hardware.

That is, the reference phase image includes the phase error which is temporally accumulated due to the resonance frequency shift and the phase error due to incompleteness of hardware, thus the two kinds of phase errors are removed from the phase difference image. Since the two kinds of phase errors undergo a gradual spatial phase change, the reference phase image represents the two kinds of phase errors with sufficient precision even if spatial resolution is low. For this reason, pre-scan for acquiring the reference phase image is sufficiently made by low spatial resolution for example, about 32*32 matrix) imaging with a short measurement time.

With the use of a multi-echo sequence which successively acquires two or more echo signals with different echo times TE, a frequency shift may be calculated from the time difference and phase difference between the echo signals, and a phase error at the intended echo time TE can be calculated from the frequency shift and removed.

In regard to the phase error due to the motion of the object, such as a blood flow, or the motion (uniform motion or accelerated motion) inside the object, a primary rephase gradient magnetic field pulse based on a known GMN (Gradient Moment Nulling) method or a higher-order rephase gradient magnetic field pulse is applied to the pulse sequence, thereby removing the effect of the motion. FIG. 4 shows an example of a rephase gradient magnetic field pulse. In order to suppress a phase error due to uniform motion (primary), with a configuration of three gradient magnetic field pulses shown in FIG. 4(a), a gradient magnetic field pulse waveform in which intensity (absolute value) is constant and the area ratio becomes 1:−2:1 is applied in the uniform motion direction. In order to suppress a phase error due to the accelerated motion (secondary), with a configuration of four gradient magnetic field pulses shown in FIG. 4(b), a gradient magnetic field pulse waveform in which intensity is constant and the area ratio becomes 1:−3:3:−1 is applied in the accelerated motion direction.

As described above, phase measured by pre-scan, multi-echo measurement, and the primary rephase gradient magnetic field pulse or higher-order rephase gradient magnetic field pulse are combined, thereby removing various phase errors from the phase difference image. For this reason, it is possible to obtain a phase difference image in which only the phase difference of the transverse magnetization, generated by short standby time (TI) after applying an RF pre-pulse, between the fluid portion labeled by the RF pre-pulse and the other stationary portion is extracted. It becomes possible then to obtain an image with enhanced contrast between the labeled fluid portion and the other stationary portion, using the phase difference.

Embodiment 1

Next, Embodiment 1 of the MRI apparatus and a fluid-enhanced image acquisition method related to the present invention will be described. The present embodiment obtains an age by shortening standby time (TI) after labeling the fluid portion by an RF pre-pulse, so as to reconstruct a contrast-enhanced image with enhanced contrast between the labeled fluid portion and the other stationary portion using phase information of the obtained image. In concrete terms, the echo signals are measured by changing the phase of the transverse magnetizations by π between the labeled fluid portion and the stationary portion, the weight coefficient for each pixel of the image is determined based on the phase image of the image reconstructed using the measured echo signals, and a fluid-enhanced image is obtained by multiplying the weight coefficient by the absolute value image for each pixel. The present embodiment will be described below in detail referring to FIGS. 5~9.

(Pulse Sequence of Embodiment 1)

Figure 5:
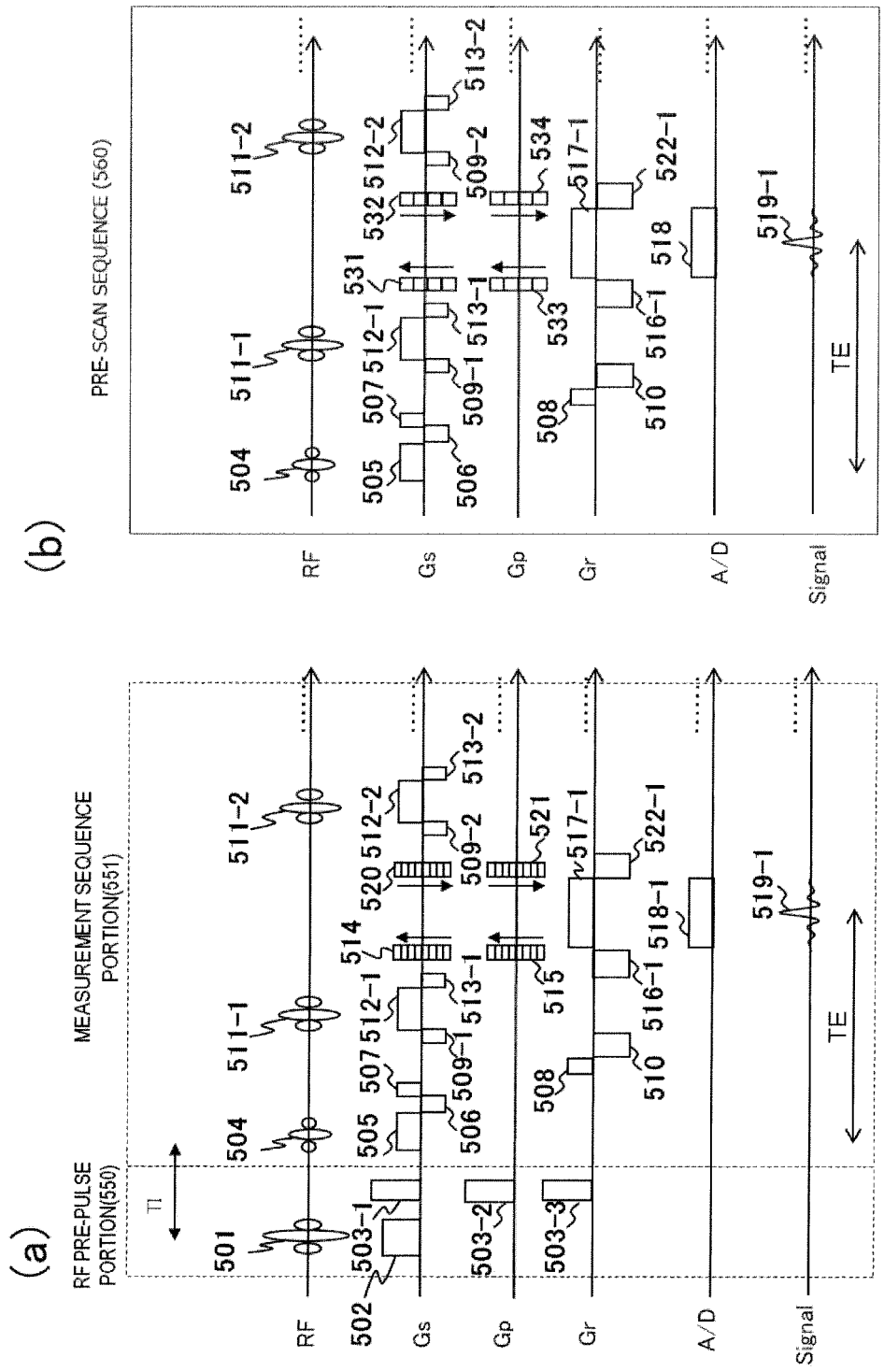
FIG. 5 shows sequence charts representing an example of a pulse sequence in Embodiment 1.

First, the pulse sequence of the invention will be described referring to FIG. 5. FIG. 5 is a sequence chart showing an example of the pulse sequence of the present embodiment, and RF, Gs, Gp, Gr, A/D and Signal respectively presents an RF pulse, a slice gradient magnetic field, a phase-encoded gradient magnetic field, a readout gradient magnetic field, a sampling period of an echo signal and an echo signal (the same in the other embodiments to be described later). FIG. 5(a) shows an example of a main scan sequence which en RF pre-pulse portion 550 which applies an IP pulse as an RF pre-pulse is provided before the measurement sequence portion 551 which uses a fast-spin echo (FSE) sequence for measurement of the echo signal for an image. FIG. 5(b) shows an example of a pre-scan sequence 560 corresponding to imaging with low spatial resolution by excluding the RF pre-pulse portion 550 from FIG. 5(a) and increasing the amount of change in the slice/phase encoded gradient magnetic field pulse in the measurement sequence portion 551. The pulse sequence to be the basis for the present embodiment is not limited to the FSE sequence, and other pulse sequences may be used. The application of the respective RF pulses of the Main-Scan sequence and the Pre-Scan sequence and the respective gradient magnetic field pulses and the measurement of echo signals are under control of the measurement control unit 111.

First, an example of a main scan sequence having the RF pre-pulse portion 550 and the measurement sequence portion 551 will be described referring to FIG. 5(a). In this main-scan sequence, standby time (TI) from application of an IR pulse 501 of the RF pre-pulse portion 550 until a transverse magnetization generating RF pulse 504 of the measurement sequence portion 551 is shortened, so that the phases of the transverse magnetization generated by the transverse magnetization generating RF pulse 504 are differentiated by π between the fluid portion labeled by the IR pulse 501 and the other stationary portion.

The RF pre-pulse portion 550 simultaneously applies the IR pulse 501 and the slice gradient magnetic field pulse 502, then applies spoiler gradient magnetic field pulses 503-1 to 503-3. The longitudinal magnetization of a desired region is selectively inversed by 180 degrees in the IR pulse 501 and the slice gradient magnetic field pulse 502. A desired region in the present embodiment is the upstream side of the fluid flown in an imaging region (FOV). In this manner, the longitudinal magnetization of the fluid portion in the upstream side region can be flipped by 180 degrees and labeled. After the IR pulse 501, spoiler gradient magnetic field pulses 503-1 to 503-3 are applied in at least one axis direction of a slice direction Gs, a phase encode direction Gp, and a readout direction Gr, preferably, in the three-axis direction, so that the transverse magnetization generated due to excitation to less than 180° by the IR pulse 501 is eliminated.

The measurement sequence portion 551 measures the echo signal on the basis of the FSE sequence. In an imaging region (FOV) which is more on the downstream side than on the upstream side that was the labeling target in the RF pre-pulse portion 550, the slice gradient magnetic field pulse 505 is applied simultaneously with a 90-degree pulse 504 which flips both the longitudinal magnetizations of the labeled fluid portion flown into the imaging region and the other stationary portion by 90 degrees. Then in order to correct the effect of the motion, primary rephase gradient magnetic field pulses 506 and 507 in which the ratio of application intensity is 1:−1:1 and the ratio of the application time is 1:2:1 are applied in the slice direction. Next, a slice gradient magnetic field pulse 512-1 applied simultaneously with a 180-degree refocus pulse 511-1, and rephase gradient magnetic field pulses 509-1 and 513-1 in which the application time is ⅙ of the slice gradient magnetic field pulse 512-1 and the intensities (absolute value) are the same are applied in the slice direction before and after application of the slice gradient magnetic field pulse 512-1.

The application of a next 180-degree refocus pulse 511-2 and slice gradient magnetic fields (509-2, 512-2 and 513-2) is to be performed in the same manner. Since the gradient magnetic field polarity to be sensed by the transverse magnetization is inversed before and after the center of the 180-degree refocus pulse 511-1, the ratio of the application area of the gradient magnetic field pulses 509, 512-1 and 513 becomes 1:−3:3:−1 to be the secondary rephase gradient magnetic field pulse. Secondary rephase gradient magnetic field pulses 508, 510, and 516-1 and a readout gradient magnetic field pulse 517-1 are applied also in the readout direction Gr.

At the center of the readout gradient magnetic field pulse 517-1, in order to detect a peak of the echo signal 519-1, if the gradient agnetic field pulses to the center of 508, 510, 516-1, and 517-1 are unitized as one gradient magnetic field pulse, the application performed so that the application is identical and the gradient magnetic field intensity ratio is 1:−3:−3:1. Similar to the slice gradient magnetic field, the intensity ratio is sensed as 1:−3:3:−1 due to the 180-degree refocus pulse 511 by the transverse magnetization, whereby obtaining the secondary rephase effect.

At the timing of the rephase gradient magnetic field pulse 516-1 in the readout direction Gr, a slice-encoded gradient magnetic field pulse 514 is applied in the slice direction Gs and a phase-encoded gradient magnetic field pulse 515 is applied in the phase encode direction Gp. After the readout gradient magnetic field pulse 517 is applied, rewind gradient magnetic field pulses 520 and 521 are applied in the slice direction Gs and the phase encode direction Gp. The gradient magnetic field pulses 514, 515, 520, and 521 are controlled so as to change for each 180-degrees refocus pulse, whereby various encodes are carried out.

At the time of the application of the readout gradient magnetic field pulse 517-1, A/D 518-1 is performed to measure an echo signal 519-1. In the readout direction Gr, if a rephase gradient magnetic field pulse 522-1 of the same form as 516-1 is applied after the application of the readout gradient magnetic field pulse, and the gradient magnetic fields of the right half of 517-1 and rephase gradient magnetic field pulse 522-1 before the next 180-degrees refocus pulse 511-2 and the left halves of rephase gradient magnetic field pulse 516-2 and readout gradient magnetic field pulse 517-2 to be subsequently repeated are unitized as one gradient magnetic field pulse, since the gradient magnetic field area ratio of 1:−3:3:−1 to be sensed by the transverse magnetization is established, the secondary rephase is repeated.

Next, the pre-scan sequence only having the measurement sequence portion 551 will be described referring to FIG. 5(b). FIG. 5(b) is an example of a pre-scan sequence corresponding to imaging with low spatial resolution when the RF pre-pulse portion 550 is excluded from FIG. 5(a), and the amount of change in the slice/phase-encoded gradient magnetic field pulses 531, 532, 533, and 534 in the measurement sequence portion 551 increases. Other parts are the same as those in the main scan sequence of FIG. 5(a), thus detailed description will not be repeated. A phase image is acquired using the echo signal measured by the pre-scan sequence, thus, as described above, it becomes possible to collectively acquire various phase errors, other than the phase difference or the transverse magnetizations between the labeled fluid portion and the other stationary portion caused by the short standby time (TI) after the IR pulsed 501 as the RF pre-pulse.

Next, preferable imaging condition in the present embodiment will be described.

First, condition of the standby time (TI) will be described. The standby time (TI) needs to be set according to an intended flow velocity ($V_b$) and an imaging region width (FOV) in the flow direction. Concretely, it is set on the basis of the equation (1).

$$TI = FOV_b / V_b \qquad (1)$$

For example, when the blood flow with about $FOV_b$=200 mm and flow velocity $V_b$=500 mm/s is targeted, the standby time (TI) is obtained as TI=400 ms by the equation (1). The TI setting of the intended flow velocity (Vb) can be uniquely determined by, for example measuring the flow velocity in advance by a phase contrast sequence, etc.

Also the measurement sequence portion needs to be performed before the longitudinal magnetization of the fluid portion which is inversed by the RF pre-pulse becomes null, the standby time (TI) is set as the upper limit value thereof (Limit TI) or lower. The Limit TI is uniquely determined by the T1 value (constant value) of the fluid and flip angle ϕ of the IF pulse, and reaches its maximum when θ=180 degrees, which needs to be:

$$TI <= \text{Limit } TI(\phi) <= \text{Limit } TI(\phi=180 \text{ degrees}) \qquad (2)$$

Next, the condition of imaging region width ($FOV_b$) in the flow direction will be described. Since the equation (1) and the equation (2) lead to:

$$FOV_b < \text{Limit } TI \times V_b \quad (3)$$

when the upper limit value is set as Limit $FOV_b$, imaging region width ($FOV_b$) in the flow direction needs to be:

$$FOV_b < \text{Limit } FOV_b = \text{Limit } TI \times V_b \quad (4)$$

Accordingly, when the standby time (TI) calculated by the equation (1) from the imaging region width ($FOV_b$) in the flow direction which is set and input by an operator surpasses the Limit TI, a message is informed to an operator to set the imaging region width ($FOV_b$) in the flow direction as the Limit $FOV_b$ or lower.

In addition, the labeling portion width (i.e., the application width of the IR pulse) in the flow direction needs to be the imaging region width ($FOV_b$) in the flow direction or greater.

As for the measurement order of the echo data to be measured in the measurement sequence portion, the centric order is preferable which first acquires the low frequency region data in the k-space that contributes to the contrast. When a known segment measurement method is applied, plural sets of segment data needs to be acquired before the labeled magnetization flown in after waiting for a TI-time completely flows out from the FOV. Therefore, it is preferable to set the upper limit value with respect to the segment number (echo train number (ETL; Echo Train Length) for a fast spin echo sequence) which is the division number of the k-space and also the echo number to be consecutively collected after application of the RF pre-pulse. The minimum repetition time minTR of the measurement sequence portion calculated from ES (Echo Space) which is the interval between the ETL and the 180-degrees RF pulse is expressed by the equation (5), and limit value Limit TR for acquiring data before flowing out can be expressed by the equation (6) using labeling width d and flow velocity Vb.

$$\min TR \rightarrow ETL * ES \quad (5)$$

$$\text{Limit max } TR = d/V_b \quad (6)$$

Limit ETL can be calculated as in the equation (7) using the equations (5) and (6).

$$\text{Limit } ETL = d/V_b/ES \quad (7)$$

For example, with application width d=200 mm of the IR pulse for labeling and the imaging condition of ES=10 msec as well as flow velocity $V_b$=500 mm/sec, the upper limit number of the segment number becomes Limit ETL number=40, and the settable echo train number is preferable to set as the upper limit number or lower. When setting an imaging condition on a set screen, the Limit ETL number may also be presented.

(Explanation of a Function Processing Unit in the Present Embodiment)

Figure 6:
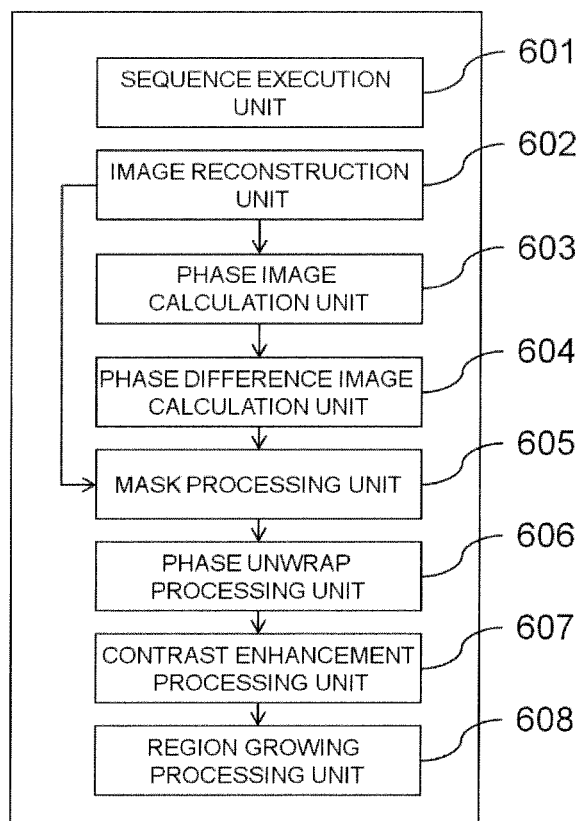
FIG. 6 is a functional block diagram of the respective functions in an arithmetic processing unit 114 of Embodiment 1.

Next, the respective arithmetic processing functions of the arithmetic processing unit 114 in the present embodiment will be described referring to FIG. 6. FIG. 6 is a functional block diagram of the respective functions in the arithmetic processing unit 114 related to the present embodiment. The respective arithmetic processing functions 114 in the present embodiment is formed by a sequence execution unit 601, an image reconstruction unit 602, a phase image calculation unit 603, a phase difference image calculation unit 604, a mask processing unit 605, a phase unwrap processing unit 606, a contrast enhancement processing unit 607 and a region growing processing unit 608. The configuration of the respective arithmetic processing functions the same in the other embodiments to be described later, a part of the processing content in the arithmetic processing function is different depending on the embodiment, which will be described in each embodiment.

The sequence execution unit 601 determines the imaging condition by confirming and correcting the imaging condition set and input by an operator, and causes the measurement control unit 111 to execute the pre-scan sequence and the main-scan sequence based on the determined imaging condition.

The image reconstruction unit 602 performs Fourier transform on the data of the echo signals (echo data) measured by both the pre-scan sequence and the main-scan sequence, and reconstructs the complex image respectively. The image reconstruction unit 602 also calculates the absolute value of the respective pixels in the complex image, whereby obtaining the absolute value image.

The phase image calculation unit 603 calculates the phase (argument) of the complex number which is the pixel value for each pixel in the complex image, whereby obtaining a phase image.

The phase difference image calculation unit 604 performs the difference operation on two phase images for each pixel, whereby obtaining the phase difference image.

The mask processing unit 605 performs the comparison operation on the pixel value and a predetermined threshold value for each pixel of the input image and converts the pixel value into a value within a predetermined range (for example, the value within 0 to 1), whereby creating a mask image. Also, the mask processing unit performs the created mask image on another image, i.e. performs a mask processing by multiplying the value of the mask image on each pixel of another image, whereby obtaining a mask-process image.

The phase unwrap processing unit 606 performs the phase unwrap processing which removes the surrounding of a principal value in each pixel value in the input phase image, whereby obtaining an unwrap-processed image.

The contrast enhancement processing unit 607 performs the contrast enhancement processing by performing the weighting operation on the absolute value image on the basis of the phase information in the phase difference image. In concrete terms, the weighting coefficient of the pixel is determined based on the pixel value (phase difference) of the respective pixels in the phase difference image, and the weighting process is performed on the pixel values by multiplying the determined weighting coefficient and the pixel value of the pixels corresponding to the absolute value image. The weighting process on the basis of the phase difference image is the contrast enhancement process, and the image after performing the contrast enhancement process is the contrast-enhanced Image.

The region growing processing unit 608 processes, on a phase image, the phase values having high continuity of phase between the adjacent pixels as the same phase. For example, when the phase difference between the adjacent pixels is within a predetermined threshold value, the phases are determined as having high continuity and set as the same phase. In concrete terms, the phase difference between the phase value of a starting point (seed point) manually set by an operator with respect to desired tissue and the phase value of the pixel which is adjacent to the starting point is compared with the threshold value, and if the phase difference is within the threshold value, the phases are determined as the same phase and set as an identical phase value region. Then if the difference between the phase value of the pixel which is adjacent to the identical phase value region and the phase value of the identical phase region is within the threshold value, the adjacent pixel is determined as having the same phase and set as the identical phase region. The previously described process is repeated to extend the identical phase region.

The processing flow of the present embodiment to be executed by the above-described respective function units in coordination will be described below with the explanation on concrete processing.

(Processing Flow of the Present Invention)

Figure 7:
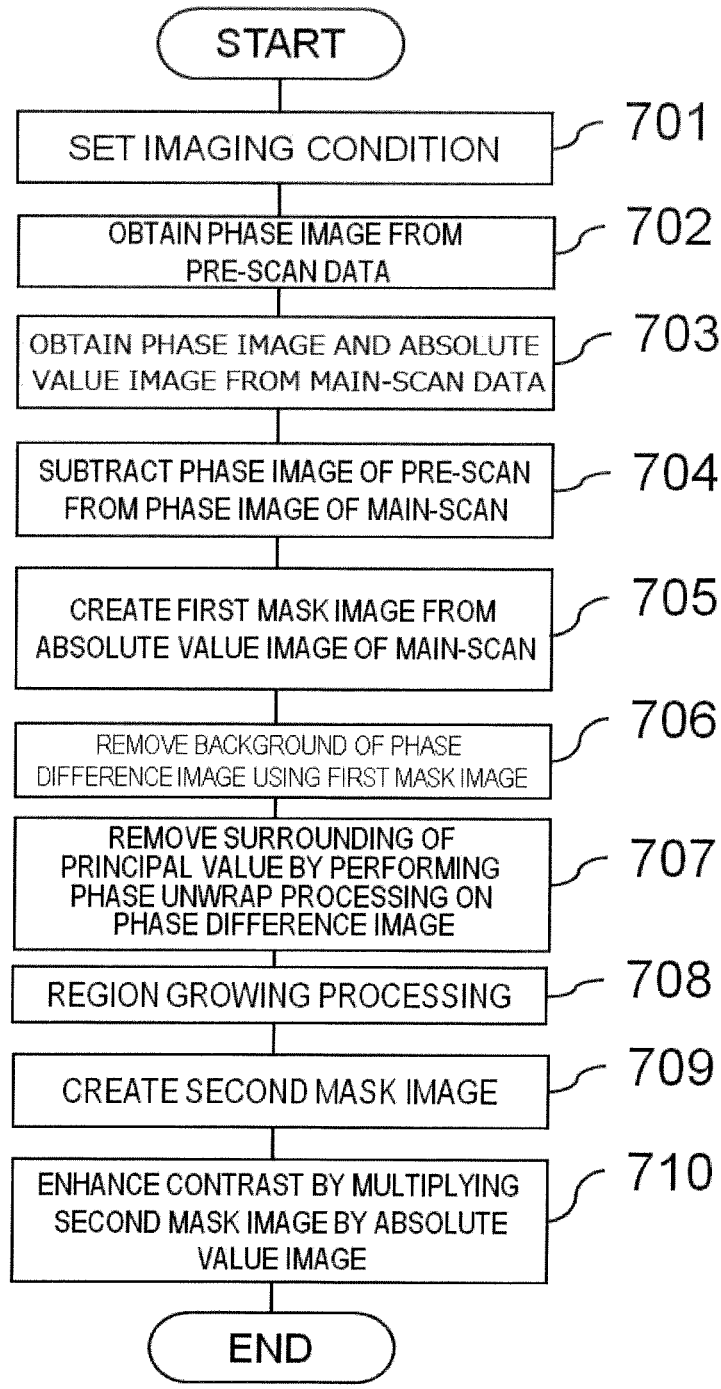
FIG. 7 is a flowchart showing the processing flow in Embodiment 1.
Figure 8:
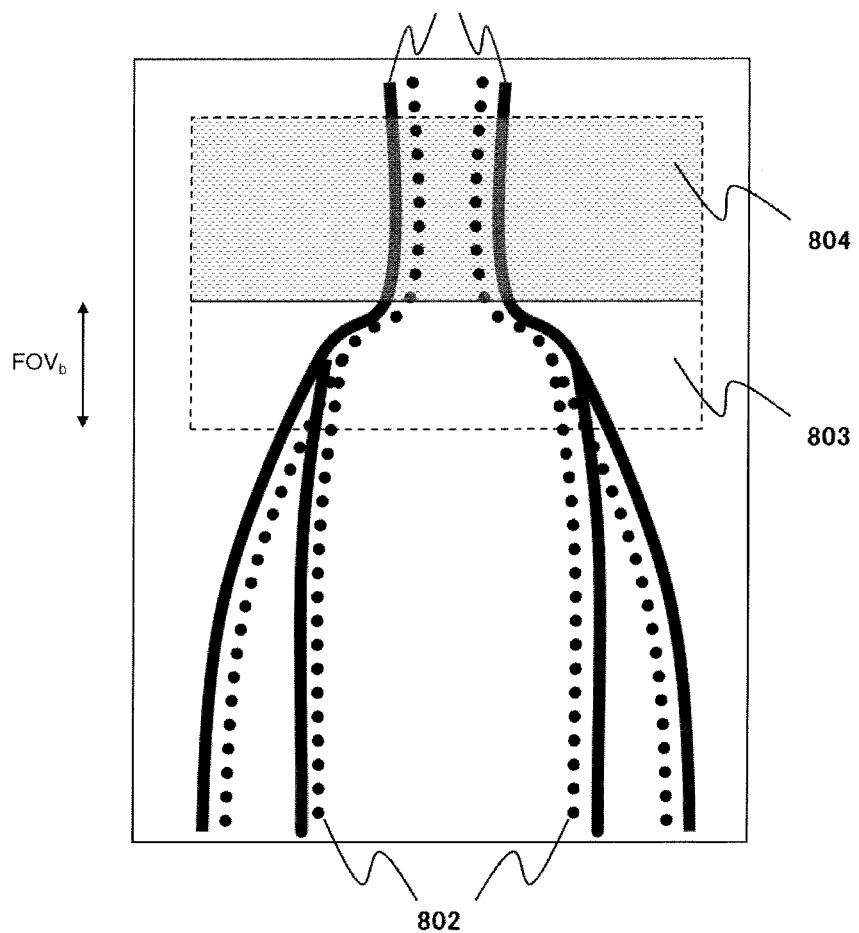
FIG. 8 is a setting example of a labeling section 804 for applying an IR pulse and an imaging section (FOV) 803 which is the downstream side of the labeling section, in Embodiment 1.
Figure 9:
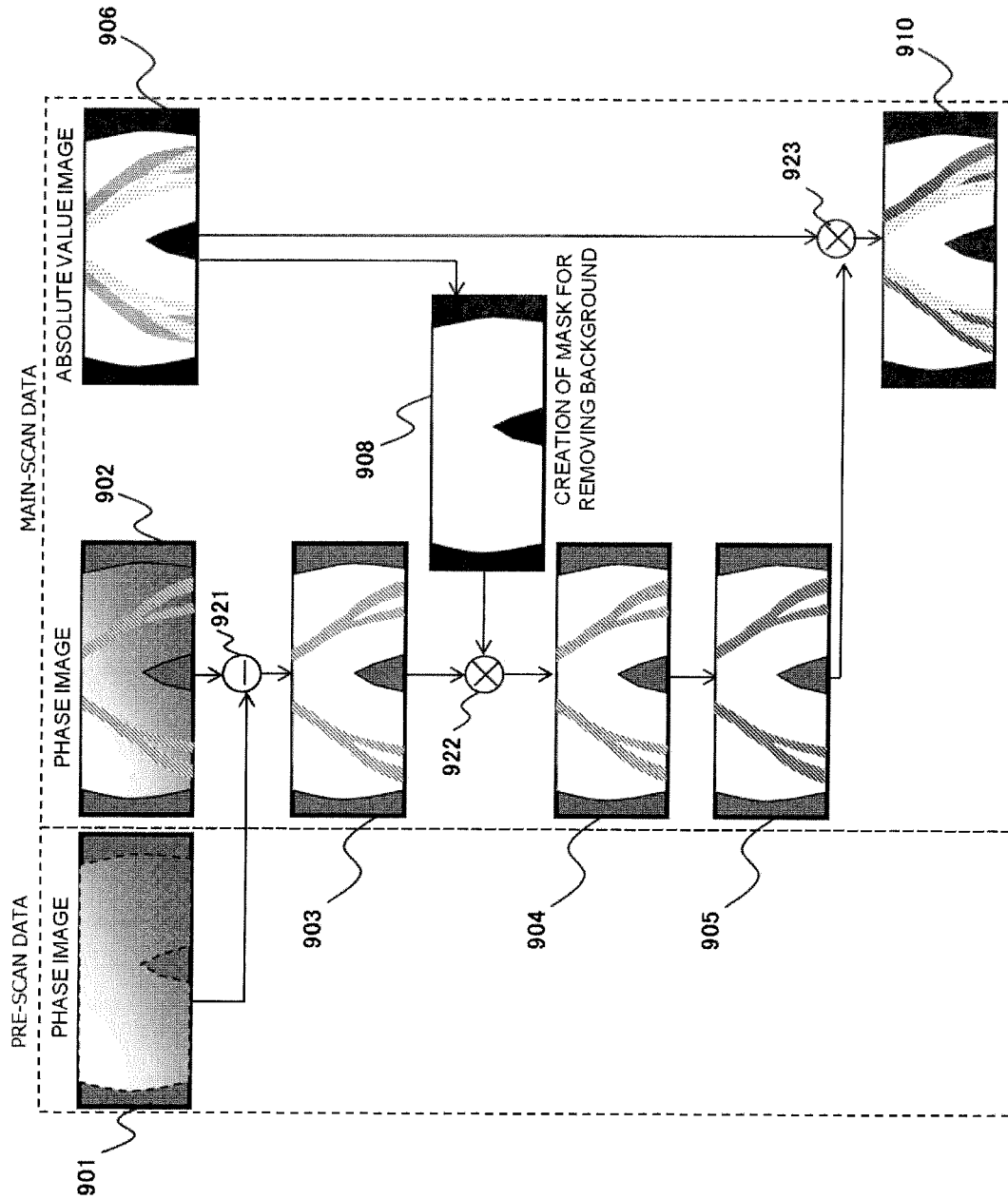
FIG. 9 is an example of the result obtained by executing the respective steps of the processing flow in Embodiment 1.

Next, the processing flow of the present embodiment will be described referring to FIG. 7. FIG. 7 is a flowchart showing the processing flow of the present embodiment. The present processing flow is to red as a program in a at age unit 115 in advance, and the arithmetic processing unit 114 reads in the program from the storage unit 115 and executes the process. Also, a lower limb region is assumed in the explanation of the present processing flow, and FIG. 8 shows a setting example of a labeling portion 804 in the upstream part wherein an IR pulse applied for labeling in the RF pre-pulse portion 550 and an imaging region (FOV) 803 which is the downstream part. Though veins (thick dotted lines) 802 flow along arteries (thick solid lines) 801 in these two regions, only the arteries 801 is to be labeled in the present embodiment. FIG. 9 shows an example of the result gained by carrying out the respective steps of the processing flow shown in FIG. 7 with respect to the respective regions shown in FIG. 8. The details of the processing in the respective steps will be described below in detail.

In step 701, the sequence execution unit 601 displays the positioning image as shown in FIG. 8, and receives the setting and input of the labeling portion 804 in the upstream part of the blood flow and the imaging region 803 in the downstream part. Then the sequence execution unit 601 checks whether or not an imaging can be performed referring to the other imaging conditions set and input by the operator. If the imaging is disapproved, the message thereof is notified to the operator, and receives the input correction of the position or the width of the labeling portion 804 and the imaging region 803 or the input correction of the other imaging conditions acquired by presenting the operator of the possible imaging condition regarding the other imaging conditions. The final possible imaging condition is determined, and various control data necessary for performing the Main-Scan sequence shown in FIG. 5(a) and the Pre-Scan sequence shown in FIG. 5(b) is calculated in concrete terms on the basis of the determined imaging condition.

In step 702, the sequence execution unit 601 notifies the measurement control unit 111 of the various control data of the Pre-Scan sequence calculated in step 701 for carrying out the Pre-Scan sequence. The measurement control unit 111 receives the command, controls the measurement of the echo signal by executing the Pre-Scan sequence, and notifies the arithmetic processing unit 114 of the data of the measured echo signal (echo data). The image reconstruction unit 602 performs Fourier transform on the echo data, and obtains a composite image with the low spatial resolution. Then the phase image calculation unit 603 acquires a phase image (first phase image) 901 of the low spatial resolution from the obtained composite image. As previously mentioned, the first phase image 901 includes various phase errors other than the phase difference between the fluid portion labeled by the IR pulse 501 and the other stationary portion.

In step 703, the sequence execution unit 601 notifies the measurement control unit 111 of the various control data of the Main-Scan sequence calculated in step 701, for executing the Main-Scan sequence. The measurement control unit 111 receives the command, controls the measurement of the echo signal by executing the Main-Scan sequence, and notifies the arithmetic processing unit 114 of the data of the measured echo signal (echo data). The image reconstruction unit 602 performs the Fourier transform on the echo data, and obtains the composite image and an absolute value image 906. Then the phase mage calculation unit 603 acquires a phase image (second phase image) 902 from the acquired composite age.

In step 704, the phase difference image calculation unit 604 converts the first phase image 901 acquired in step 702 into the phase image having the same spatial resolution as the second phase image 902 which is acquired in step 703, and performs difference processing 921 between the converted image and the second phase image 902, whereby obtaining a phase difference image 903. The obtained phase difference image 903 is the phase image from which the phase error due to resonance frequency shift and the phase error due to incompleteness of hardware are removed, as well as the phase image on which only the phase difference generated by short standby time (TI) after the IR pulse 501 is reflected.

In step 705, the mask processing unit 605 creates a first mask image 908 for extracting only an object region in the absolute image 906, by setting a threshold value (for example, 20% of the maximum value within each pixel value) with respect to the pixel value (absolute value) in the respective pixels of the absolute value image 906 obtained in step 703 and removing the pixel having the pixel value which is smaller than the set threshold value as background (noise region). In concrete terms, the first mask image 908 is created by respectively allotting 0 to the pixel having the pixel value which is smaller than the threshold value and allotting 1 to the pixel having the pixel value greater than the threshold value.

In step 706, the mask processing unit 605 performs the first mask image 908 created in step 705 on the phase difference image 903 obtained in step 704, i.e. executing a mask processing 922 which multiplies the phase difference image 903 by the first mask image 908 for each pixel, and creates a phase difference image 904 wherein the background region is removed and only the object region is extracted from the phase difference image 903. On the pixel values (phase values) of the removed background region, a predetermined steady value (for example, 0) is allotted. In addition, since the value of the background region in the first mask image 905 is 0, the value of the background region in the result image in which the multiplication is performed by pixels inevitably becomes 0.

In step 707, the phase unwrap processing unit 606, with respect to the phase difference image 904 which mask-processed in step 706, performs the phase unwrap processing which removes the surrounding of the principal value. Further, by setting the phase value of the stationary portion as reference phase $\theta_{ref}$, difference $(\theta-\theta_{ref})$ is acquired in which reference phase $\theta_{ref}$ is subtracted from the phase value $\theta$ of all pixels, i.e. the reference phase is evenly subtracted from the respective pixel values in the phase difference image, so as to create a corrected phase difference image. The corrected phase difference image represents the difference phase from the phase values in the stationary portion, wherein the phase in the stationary portion is 0 and the phase in the labeled blood flow portion is $\pi$.

In step 708, the region growing processing unit 608 performs the region growing process with respect to the corrected phase difference image obtained in step 707. A starting point (seed point) is manually set by the operator with respect to desired tissue, and the region growing process is executed starting from the starting point, so as to collect the pixels which can be determined as having the same phase value as that of the starting point to create an identical phase value region. As a result of the region growing process, the phase the respective pixels in the identical phase value region on the corrected phase difference image can be replaced with the phase value of the starting point. In addition, the processing in the present step 708 may also be omitted.

In step 709, the contrast enhancement processing unit 607 determines the weighting coefficient of the pixel based on the pixel value (phase value) in the respective pixels of the corrected phase difference image obtained in steps 707 or 708, and creates a second mask image 905 which represents the distribution of the determined weighting coefficient. In concrete terms, with respect to the pixel value of the respective pixels in the corrected phase difference image obtained in step 707, a predetermined threshold value (for example, $\pm\pi/2$) is set. The absolute value of phase value $\theta$ which is the pixel value that is less than the threshold value (that is, $-\pi/2<\theta<+\pi/2$) is converted into 1, the absolute value of the other case (that is, $[\theta \le -\pi/2]$ or $[+\pi/2 \le \theta]$) is converted into the value of [0~1], and the converted values are set as the weighting coefficient of the pixel. By this conversion, the phase of the labeled blood flow portion is converted into the weighting coefficient of [0~1] (for example, 0.5), and the phase of the stationary portion is converted into the weighting coefficient of 1, respectively. The weighting coefficient is determined in the similar manner with respect to all pixels of the corrected phase difference image, and the second mask image 905 is created which represents the distribution of weighting coefficient in the respective pixels. The second mask image 905 becomes the contrast-enhancing mask mage.

In step 710, the contrast enhancement processing unit 607 performs the second mask image (contrast-enhancing mask image) 905 obtained in step 709 on the absolute value image 906 obtained in step 703 (923). In concrete terms, the weighting process is performed on the pixel value of the respective pixels in the absolute value image 906 using the pixel value in the second mask image 905, by multiplying the pixel values of the absolute value image 906 by the pixel values of the second mask Image 905 for each of the identical pixels (923). The weighting process using the second mask image 905, i.e. based on the phase difference image 903 (923) is the contrast enhancing process, and a contrast-enhanced image 910 is obtained by this contrast enhancing process.

In the contrast-enhanced image 910, the blood flow (artery) region which is labeled with respect to the stationary region is suppressed. In other words, in the absolute value image 906, the contrast between the labeled blood flow (artery) region and the other stationary region is enhanced. In the example of the contrast-enhanced image 910 shown in FIG. 9, the signal in the labeled blood flow (artery) region is suppressed, and the luminance only in the other stationary region is enhanced.

The processing flow of the contrast-enhanced image acquisition method in the present embodiment has been described above.

In accordance with the above-described configuration, the MRI apparatus and the fluid-enhanced image acquisition method of the present embodiment sets short standby time (TI) from application of an Ft pre-pulse to execution of a measurement sequence, whereby reducing the imaging time. Furthermore, by acquiring the phase difference image by setting the phase difference by n between a blood flow portion to be labeled and the other stationary portion and performing weighting on the absolute value image on the basis of the acquired phase difference image, it is possible to obtain an image in which the contrast between the labeled blood flow portion and the other stationary portion is further enhanced compared to the method of creating contrast by extending the standby time and by only the signal intensity difference.

Also, while the weighting coefficient is determined so that the signal of the stationary portion is suppressed with respect to the signal of the blood flow portion in the previously described step 709, the weighting coefficient may also be determined the other way around so that the signal of the stationary portion is suppressed with respect to the signal of the blood flow portion. In concrete terms, the pixel value may be converted into [0~1] when the absolute value of pixel value (phase value) $\theta$ in the respective pixels of the corrected phase difference image is less than the threshold value (that is, $-\pi/2<\theta<+\pi/2$) and the pixel value may be converted into the value of 1 in the other case (that is, $[\theta \le -\pi/2]$ or $[+\pi/2 \le \theta]$), to be set as the weighting coefficient of the pixels.

As described above, the MRI apparatus and the fluid-enhanced image acquisition method in the present embodiment, using a pulse sequence formed by an RF pre-pulse portion comprising an RF pre-pulse (IR pulse) which excites the longitudinal magnetization of a fluid portion in a negative direction and performs labeling on the fluid portion and a measurement sequence portion which measures the echo signal from an imaging region into which the labeled fluid portion is flown, performs labeling by applying the RF pre-pulse to the region upstream of the imaging region and exciting the longitudinal magnetization of the fluid portion in a negative direction, measures the echo signal from the imaging region before the longitudinal magnetization in the labeled fluid portion recovers to null, and obtains an image with enhanced contrast of the fluid portion with respect to a stationary portion based on phase information of the image which is reconstructed using the measured echo signal. As a result, it is possible to obtain an image with enhanced contrast between a blood flow portion and a stationary portion while reducing the imaging time, even when an IR pulse is used as an RF pre-pulse.

Embodiment 2

Next, Embodiment 2 of the MRI apparatus and the fluid-enhanced image acquisition method related to the present invention will be described. In the present embodiment, an RF pre-pulse portion has two RF pre-pulses with different flip angles, and the labeling is performed with respect to two fluid portions having different flow directions (for example, an artery and a vein) by irradiating the respective RF pre-pulses to the regions of the upstream side and the downstream side in the fluid portion with an imaging region (FOV) therebetween. In this manner, it is possible to obtain an image having different contrast not only between the fluid portion and the stationary portion but also between two fluid portions. The two RF pulses are, for example the IR pulses having different flip angles, and the contrast enhancement can be differentiated between two fluid portions having different flow directions by having different flip angles. The present embodiment will be described below in detail referring to FIGS. 10~12, setting the RF pre-pulse as an IR pulse and setting two fluid portions having different flow directions as an artery and a vein.

First, an RF pre-pulse portion in Embodiment 2 will be described. By setting flip angle $\phi_1$ of one IR pulse of the two IR pulses in the RF pre-pulse portion (hereinafter referred to as $IR_1$) is set as $90°<\phi_1<270°$ (preferably, $\phi_1=180°$), the contrast of the blood flow portion to be labeled by the $IR_1$ is enhanced on the basis of the phase difference, as in the previously described Embodiment 1. The flip angle $\phi_2$ of the other IR pulse (hereinafter referred to as $IR_2$) is set as $0°<\phi_2\leq90°$ (preferably, $\phi_2=90°$, the contrast of the blood flow portion to be labeled by the $IR_2$ is enhanced on the basis of the signal intensity difference.

Then as the imaging condition related to standby time (TI), standby time $TI_1$ in particular corresponding to $IR_1$ needs to be shorter than the time that the longitudinal magnetization excited by flip angle $\phi_1$ recovers by T1 to null, that is:

$$TI_1 < \text{Limit } TI(\phi_1) < \text{Limit } TI(\phi_1 = 180°).$$

Standby time $TI_2$ corresponding to $IR_2$ is to be set as the time that the longitudinal magnetization of the blood flow portion to be labeled by $IR_2$ recovers by $T_1$ to be a desired signal intensity. The respective pulses are applied in order of $IR_2$-$IR_1$ when $TI_1<TI_2$, and in order of $IR_1$-$IR_2$ when $TI_1>TI_2$.

Also, the velocity of an artery and a vein is set as Vba and Vbv respectively as the imaging condition regarding the imaging region width ($FOV_b$) in the flow direction, in the case of labeling the artery by $IR_1$ and the vein by $IR_2$ respectively, upper limit value Limit $FOV_b$ of the imaging region width ($FOV_b$) in the flow direction is expressed by:

$$FOV_b < \text{Limit } FOV_b = \text{MIN}((Vba \times TI_1),(Vbv \times TI_2)). \quad (8)$$

On the contrary, when the vein is labeled by $IR_2$ and the vein by $IR_1$ respectively, the FOVb is expressed by:

$$FOV_b < \text{Limit } FOV_b = \text{MIN}((Vba \times TI_2),(Vbv \times TI_1)). \quad (9)$$

Here, MIN(a,b) is set as the function which represents the smaller one of a and b. Since Vba>Vbv in general, it is preferable that the labeling order is set to perform labeling on the vein and on the artery next in light of acquiring a wide imaging region width ($FOV_b$) in the flow direction, thus Limit $FOV_b$ of the vein is first determined by the equation (8) when labeled by $IR_2$ to be ($TI_1<TI_2$) and by the equation (9) when labeled by $IR_1$ to be ($TI_1>TI_2$) respectively.

The case that the vein is first labeled by $IR_1$ then the artery is labeled by $IR_2$ will be described below. In this case, the relationship among the standby times is: Limit $TI>TI_1>TI_2$. In addition, it is also possible to label the artery first by $IR_1$ or $IR_2$.

Figure 10:
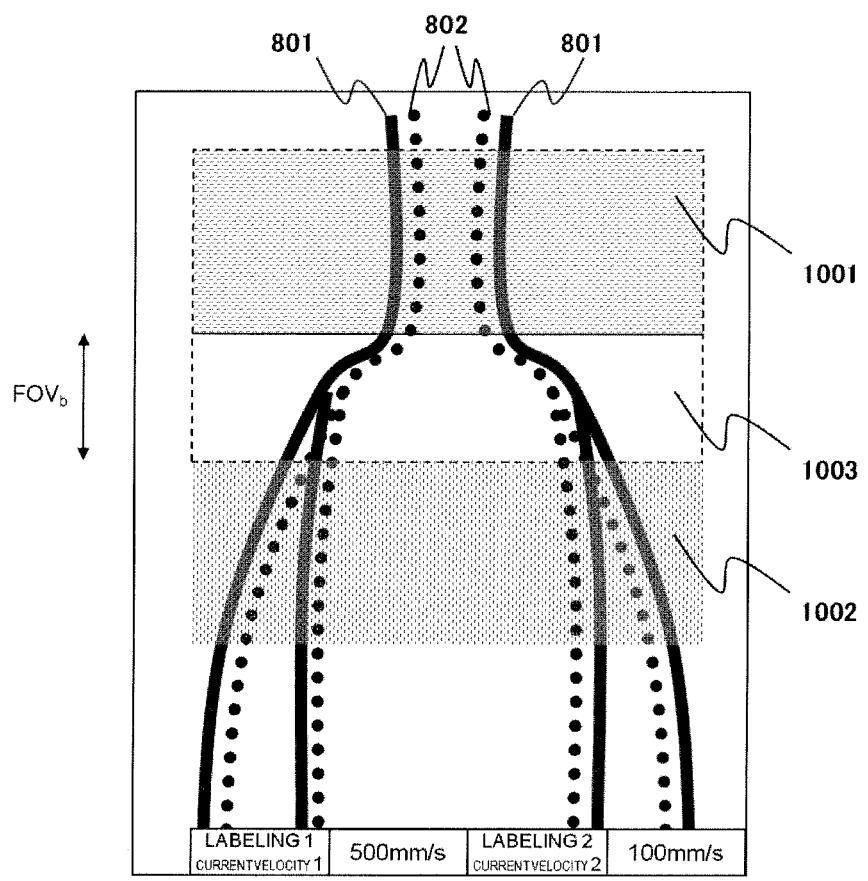
FIG. 10 is a setting example in Embodiment 2 of a labeling section by the respective IR pulses in a lower extremity region.

Next, setting of a labeling portion in the present embodiment will be described referring to FIG. 10. FIG. 10 shows a setting example of a labeling portion by the respective IR pulses with respect to an artery (solid line) 801 and a vein (dotted line) 802 in a lower limb region. In order Co perform labeling on the vein by IR1($\phi_1=180°$), a labeling portion 1002 by $IR_1$ is set in the upstream side in relation to the vein (downstream side in relation to the artery), a labeling portion 1001 by $IR_2$ is set in the upstream side in relation to the artery (downstream side in relation to the vein), and an imaging region (FOV) 1003 is set between the labeling portions 1001 and 1002. In this manner, an operator sets the respective labeling portions and an imaging region on a positioning image. Further, as shown in FIG. 10, the operator may input an intended velocity of the labeling for each labeling portion on the positioning image, so that the imaging region width ($FOV_b$) in the flow direction can be optimized on the basis of the equations (8) and (9). After the optimal imaging region width ($FOV_b$) in the flow direction is acquired and set, the adjustment of the position and width of the respective labeling portions is performed manually by the operator or automatically by the apparatus. On the contrary, the artery may be labeled by exciting the labeling portion 1001 with $IR_1$ and the vein may be labeled by exciting the labeling portion 1002 with $IR_2$.

Next, the pulse sequence in the present embodiment will be described. Since the pulse sequence in the present embodiment is formed by the Main-Scan sequence and the Pre-Scan sequence as the pulse sequence in the previously described Embodiment 1, and the Pre-Scan sequence is the same as the previously described Embodiment 1, thus the description thereof will not be repeated.

Figure 11:
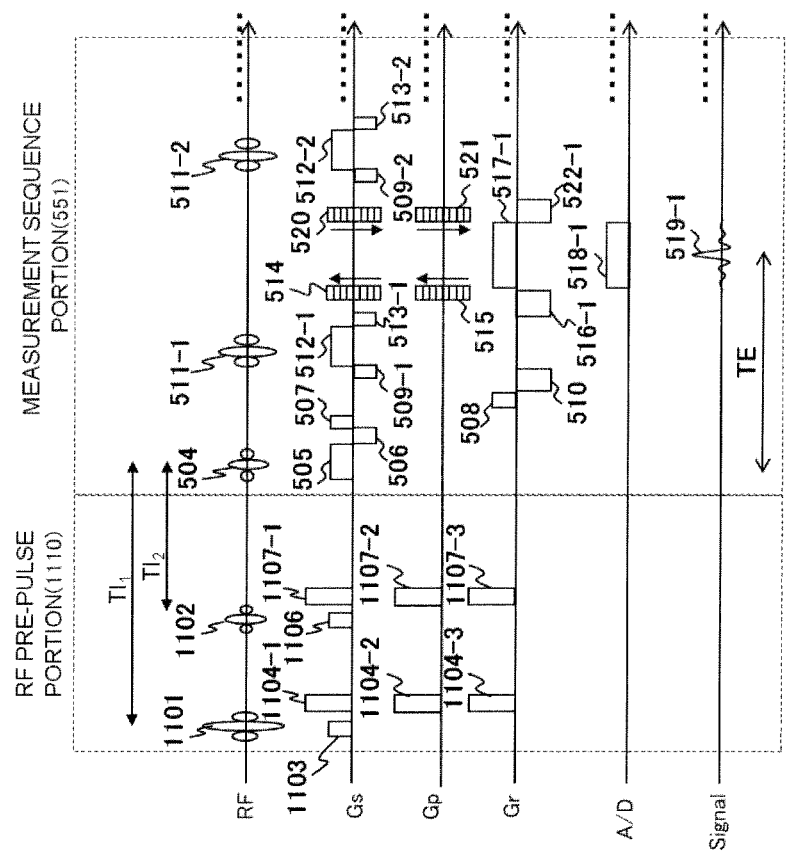
FIG. 11 is a sequence chart of a Main-Scan sequence in Embodiment 2.

An example of the Main-Scan sequence in the present embodiment will be described using the sequence chart shown in FIG. 11. The Main-Scan sequence shown in FIG. 11 is formed by an RF pre-pulse portion 1110 including two IR pulses (1101 and 1102) having different flip angles and standby times and the measurement sequence portion 551. The measurement sequence portion 551 is the same as the previously described Embodiment 1, thus the detailed description thereof will be omitted, and the RF pre-pulse portion 1110 will be described below in detail.

In the OF pre-pulse portion 1110, the IR pulse 1101 which is equivalent to $IR_1$ (for example, flip angle $\phi_1=180°$) and a slice gradient magnetic field 1103 are simultaneously applied first and the labeling portion 1002 in FIG. 10 is excited, so that the blood flow of the vein is labeled. The IR pulse 1101 at this point is set as Sinc-wave having the resonance frequency and the frequency band of the labeling portion 1002 which is determined by the slice gradient magnetic field 1103. Then spoiler gradient magnetic field pulses (1104-1~1104-3) are applied to three axes after the IR pulse 1101, and the transverse magnetization which is generated by the excitation by the IR pulse 1101 at less than 180° is eliminated.

Next, the IR pulse 1102 which is equivalent to $IR_2$ (for example, flip angle $\phi_1=90°$) and a slice gradient magnetic field 1106 are simultaneously applied and the labeling portion 1101 is excited, so that the blood flow of the artery is labeled. The IR pulse 1102 at this time is set as Sinc-wave having the resonance frequency and the frequency band of the labeling portion 1011 which is determined by the slice gradient magnetic field 1106. Then spoiler gradient magnetic field pulses (1107-1~1107-3) are applied to three axes after the IR pulse 1102, and the transverse magnetization which is generated by the IR pulse 1102 is eliminated.

In addition, two spoiler gradient magnetic field pulses (1104 and 1107) may be put together as one pulse for each axis and applied at one time.

Then a transverse magnetization generating RF pulse 504 of the measurement sequence portion 551 is applied at the timing that the standby time from the IR pulse 1101 is $TI_1$ and the standby time from the IR pulse 1102 is $TI_2$, and the measurement sequence portion 551 is started.

Figure 12:
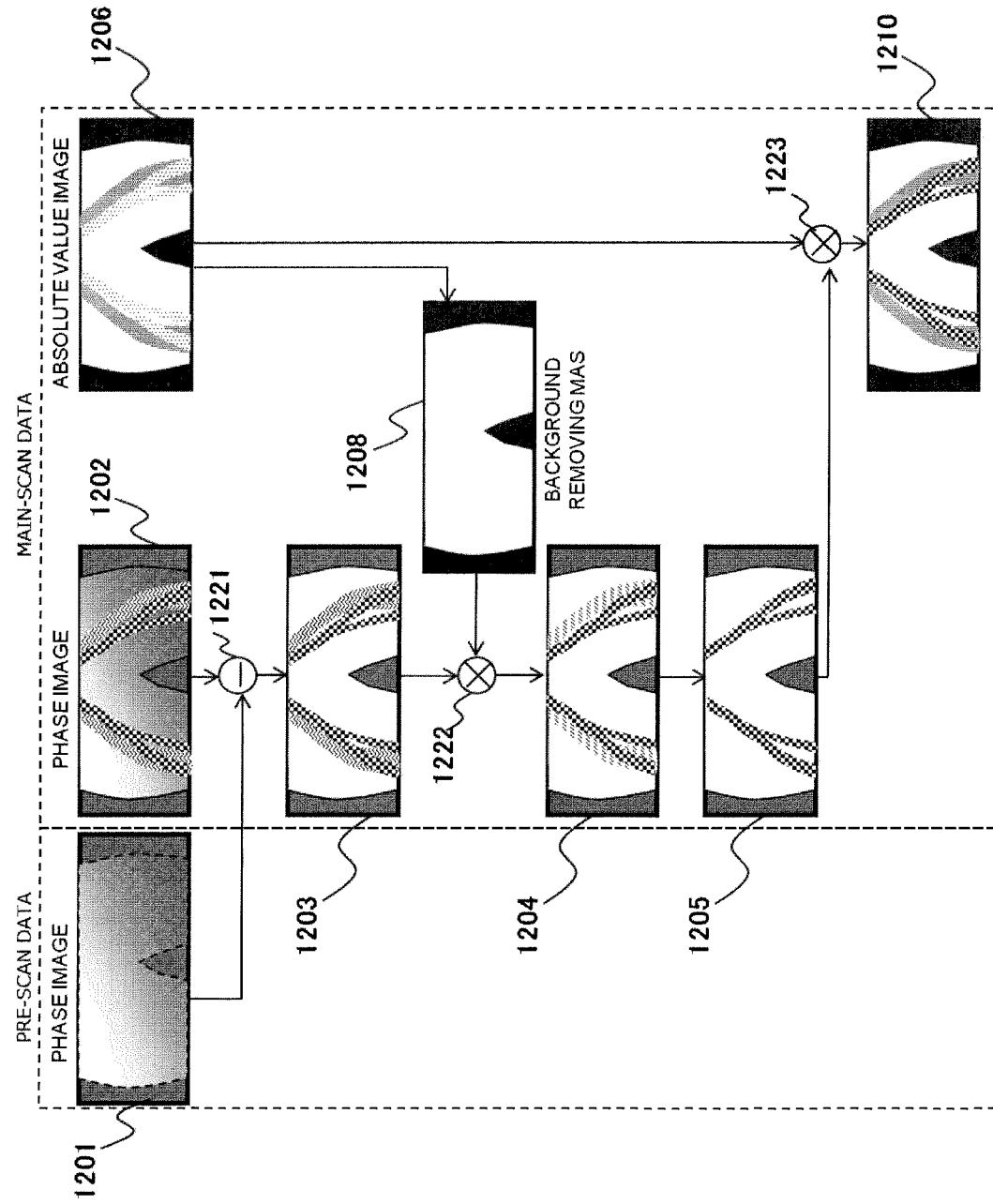
FIG. 12 is an example of the result obtained by executing the respective steps of the processing flow in Embodiment 2.

Next, the processing flow in the present embodiment will be described. While the processing flow in the present embodiment is the same as the processing flow based on the flowchart shown in FIG. 7 which is described in Embodiment 1, a part of the processing in some steps is different, thus only the processing steps that are different from Embodiment 1 will be described below. Also, FIG. 12 shows an example of the result obtained by performing the respective steps in the processing flow shown in FIG. 7. In order to indicate clearly that the step numbers below corresponding to FIG. 7 are of the present embodiment, "-2" will be added to the step numbers.

In step 701-2, the sequence execution unit 601 displays the positioning image as shown in FIG. 10, and receives the setting and input of the labeling portion 1001 in the upstream side of the artery, the labeling portion 1002 in the upstream side of the vein and the imaging region 1003 which is placed between the previous two regions. Then the sequence execution unit 601 checks whether or not an imaging can be performed referring also to the other imaging conditions set and input by the operator. If the imaging is disapproved, the sequence execution unit 601 notifies the operator the message thereof, and receives the correction and input of the position or the width of the labeling portions 1001, 1002 and the imaging region 1003 or the correction and input of the other imaging conditions acquired by presenting the operator of the possible condition regarding the other imaging conditions. The final possible imaging condition is determined, and various control data necessary for performing the Main Scan sequence shown in FIG. 11 and the Pre-Scan sequence shown in FIG. 5(*b*) is calculated in concrete terms on the basis of the determined imaging conditions. Particularly, the IR pulse 1101 and the slice gradient magnetic field 1103, and the IR pulse 1102 and the slice gradient magnetic field 1106 respectively correspond to the Sinc-wave and the gradient magnetic field intensity, wherein the resonance frequency and the frequency band are set in the Sinc-wave, so that the labeling portion 1002 for the vein and the labeling portion 1001 for the artery are respectively and independently excited.

In step 702-2, the same processing is executed as step 702 in the previously described Embodiment 1. As a result, a phase image (first phase image) 1201 of the low spatial resolution is obtained. This first phase image 1201 includes various phase errors other than the phase difference between the vein which is labeled by the IR pulse 1101 and the IR pulse 1102 respectively, and the blood flow portion of the artery and the other stationary portion.

In step 703-2, the same processing as step 703 in the previously described Embodiment 1 is executed. As a result, the composite image and the absolute value image 1206 is obtained, and the phase image (second phase image) 1202 is obtained from the composite image.

In step 704-2, the same processing as step 704 in Embodiment 1 is executed. That is, the phase difference image calculation unit 604 first converts the first phase image 1201 obtained in step 702-2 into the phase image of the same spatial resolution as the second phase image 1202 which is obtained in step 703-2, then executes a difference processing 1221 between the second phase image 1202 and the converted first phase image 1201, thereby obtaining a phase difference image 1203. The phase difference image 1203 is the phase image from which the phase error due to the resonance frequency displacement and the phase error due to the incompleteness of the hardware is removed, and on which only the phase difference generated by short standby time ($TI_1$) after the IR pulse 1101 is reflected.

In step 705-2, the same processing as step 705 in Embodiment 1 is executed. As a result, a first mask image 1208 is obtained.

In step 706-2, the same processing as step 706 in Embodiment 1 is executed. That is, the mask processing unit 605 performs the first mask image 1208 created in step 705-2 on the phase difference image 1203 obtained in step 704-2 (1222), thereby obtaining a phase difference image 1204 from which the background region (noise region) is removed and only an object region is extracted from the phase difference image 1203.

In step 707-2, the same processing as step 707 in Embodiment 1 is executed. As a result, in the corrected phase difference image, the phase of the blood flow portion (artery) which is labeled in the stationary portion by $IR_2$ is zero and the phase in the blood flow portion (vein) which is labeled by $IR_1$ is $\pi$.

In step 708-2, the same processing as step 706 in the previously described Embodiment 1 is executed.

In step 709-2, the same processing as step 709 in Embodiment 1 is executed. As a result, a second mask image 1205 is obtained. For example, the second mask image 1205 can be set for weighting with the intensity ratio of the vein, artery and stationary portion as 0:1:1 respectively. In other words, the second mask image 1205 is for enhancing the contrast among the vein, artery and stationary portion based on the phase difference among the vein, artery and stationary portion.

In step 710-2, the same processing as step 710 in the previously described Embodiment 1 is executed. That is, the contrast enhancement processing unit 607 performs the second mask image 1205 obtained in step 709-2 on the absolute image 1206 obtained in step 703-2 (1223), thereby obtaining a contrast-enhanced image 1210.

The contrast-enhanced image 1210 is the image in which the labeled blood flow portion (the artery and the vein) is suppressed with respect to the stationary portion. In concrete terms, the weighting is performed on the vein 802 by the second mask image 1205 on the basis of the phase difference between the artery and the stationary portion, with the intensity ratio of 0:1. The weighting is also performed on the artery 801 between the artery and the stationary portion based on the signal intensity difference in the absolute value image 1206 with the signal intensity ratio of, for example 0.5:1. Then as a result of both weighting processes, the contrast-enhanced image 1210 is obtained in which the intensity ratio among the vein, artery and stationary portion is enhanced by 0:0.5:1 respectively. That is, not only the contrast between the labeled blood flow portion (the artery and the vein) and the stationary portion, but also the contrast between the artery 801 and the vein 802 is enhanced in the image.

In addition, since the absolute value image 1206 and the phase difference images (1203 and 1204) correspond to the artery-enhanced image and the vein-enhanced image respectively which makes it easy to extract the respective regions, it is also possible to perform arbitrary coloring on the artery 801 and the vein 802.

The processing flow in the present embodiment has been described above. While the case in which the phase difference of the vein 802 is enhanced using $IR_1$ and the signal intensity difference of the artery 801 is enhanced using $IR_2$ has been described above, the phase-difference enhancement may also be performed on the artery 801 by labeling using $IR_1$ and the signal intensity difference may also be enhanced by labeling the vein 802 using $IR_2$, and the same processing can be applied to this case.

As described above, the MRI apparatus and the fluid-enhanced image acquisition method in the present embodiment has a first fluid portion (vein) and a second fluid portion (artery) of which the flow directions are different, wherein an RF pre-pulse portion includes a first RF pre-pulse ($IR_1$) and a second RF pre-pulse ($IR_2$) of which the flip angles are different, and is capable of obtaining a fluid-enhanced image by labeling the first fluid portion by applying the first RF pre-pulse to a first region in the upstream side of the first fluid portion (labeling portion 1002), labeling the second fluid portion by applying the second RF pre-pulse to a second region upstream of the second fluid portion (labeling portion 1001), setting the region between the first region and the second region as an imaging region, and differentiating the contrast between the first fluid portion and the second fluid portion. In this manner, the blood flow portions (an artery and a vein) which the flow directions are different can be enhanced with different contrast from a stationary portion as well as enhancing the contrast between the artery and the vein without increasing the imaging time, thereby obtaining the image in which not only the artery and the Sin but also the fluid portion and the stationary portion can be clearly distinguished in a short period of time. That is, an artery and a vein can be depicted separately.

Embodiment 3

Next, Embodiment the MRI apparatus and the fluid-enhanced image acquisition method related to the present invention will be described. The present embodiment performs labeling using the 2-dimensional spatially-selective excitation. The labeling method in the previously described Embodiment 2 combined an IN pulse and a slice gradient magnetic field pulse and excited the region having a predetermined width in the direction which is vertical to the flow direction, for labeling the fluid portion which passes through the excited region. However, the excitation is performed by this method not only on the fluid region which passes through the labeling portion, but also on the stationary portion on which excitation is not necessary. For this reason, Embodiment 3 performs the 2-dimensional spatially-selective excitation capable of selectively exciting the fluid portion. Further, the present embodiment performs the 2-dimensional spatially-selective excitation at different flip angles on the fluid portions at different positions, for labeling the fluid portions respectively. In concrete terms, one fluid portion is labeled using 2-dimensional spatially-selective $IR_1$, and the other fluid portion is labeled using 2-dimensional spatially-selective $IR_2$. Only one fluid portion may also be labeled by performing 2-dimensional spatially-selective excitation. The present embodiment will be described below in detail exemplifying an artery as a fluid portion, referring to FIGS. 13~16.

Figure 13:
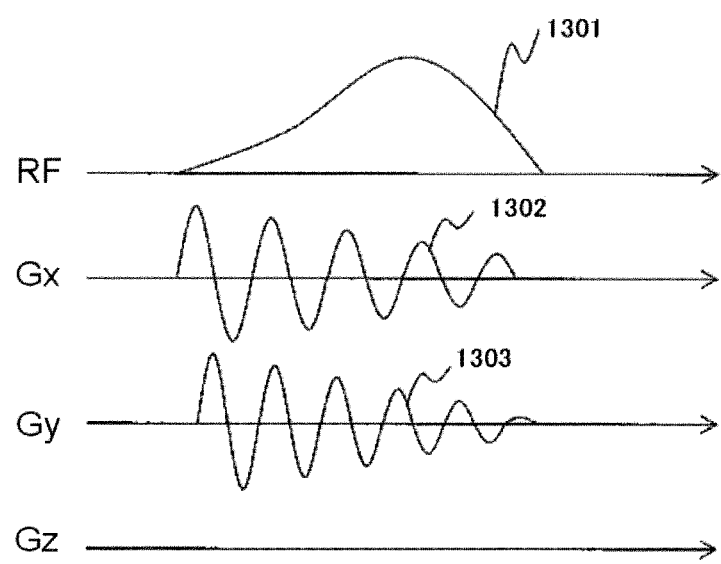
FIG. 13 is an example of 2-dimensional space selective excitation in Embodiment 3 which selectively excites a columnar region in the z-direction wherein only the shape on the xy-plane is specified.

First, the outline of the 2-dimensional spatially-selective excitation will be described using FIG. 13. FIG. 13 shows an example that a columnar region is selectively excited in the z-direction in which only the shape on the x-y plane is specified is selectively excited. The shape which is specified on the x-y plane is a circle. RF, Gx, Gy and Gz respectively indicate the application timing of an RF pulse, a gradient magnetic field in the x-axis direction, a gradient magnetic field in the y-axis direction and a gradient magnetic field in the z-direction. As shown in FIG. 13, an RF pulse (2DRF) 1301 is applied along with an oscillating gradient magnetic field (Gx) 1302 in the x-axis direction and an oscillating gradient magnetic field (Gy) 1303 in the y-axis direction. By this application, a cylinder-shaped region which is parallel with the z-axis is selectively excited. At the time of performing 2-dimensional spatially-selective excitation by combining the RF pulse and the gradient magnetic field pulses as described above, the adjustment of the shape, position and flip angle is performed by controlling the frequency and waveform of the RF pulse and the waveform of the gradient magnetic field pulses. Hereinafter, the labeling using 2-dimensional spatially-selective excitation is referred to as spatially-selective labeling. The detailed explanation on 2-dimensional spatially-selective excitation provided in Non-patent Document 2, thus the detailed explanation thereof will not be repeated below.

Figure 14:
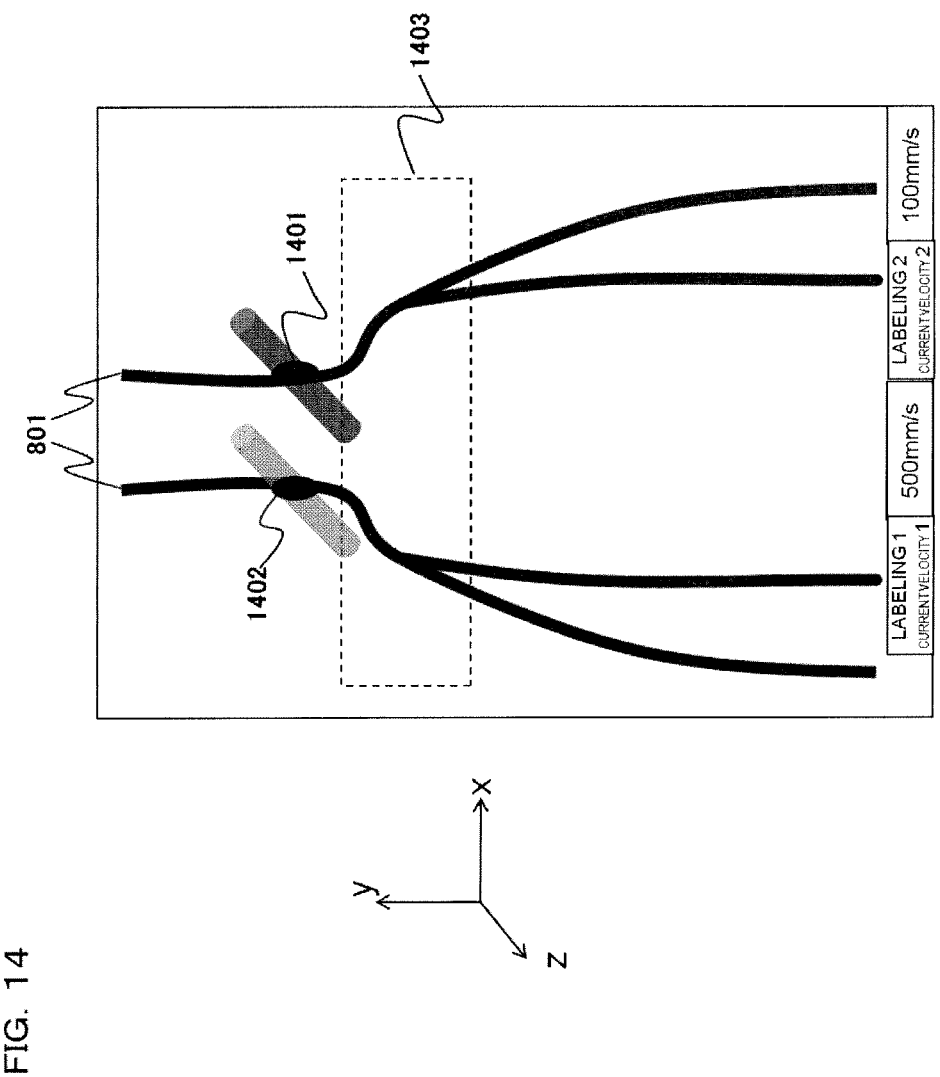
FIG. 14 is a setting example in Embodiment 3 of a region for performing spatial selective labeling on each of artery 801 on the right and left in a lower limb region.
Figure 15:
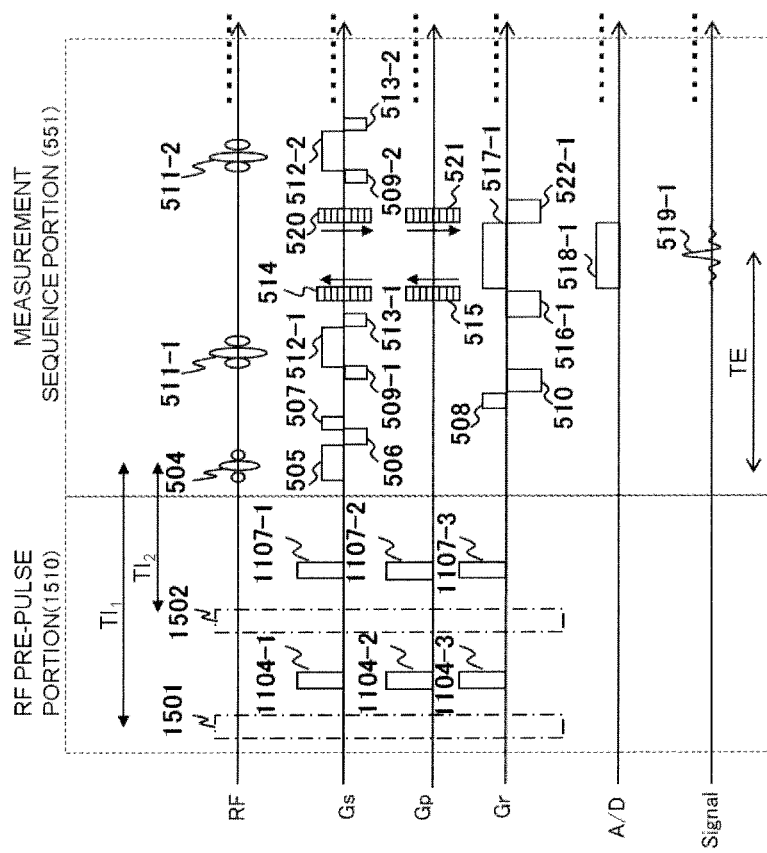
FIG. 15 is a sequence chart of an RF pre-pulse portion in Embodiment 3.

Next, setting of a region for performing spatially-selective labeling, which is related to the present embodiment, will be described referring to FIG. 14. FIG. 14 shows a setting example of a region on which the spatially-selective labeling of the present embodiment is performed on each of the left and right arteries 801 in a lower limb region. The spatially-selective labeling (hereinafter referred to as 2D-$IR_1$) performed on the longitudinal magnetization in the upstream region of an artery 1401 on the right side by flip angle $\phi_1$ (for example, 180°), and the spatially-selective labeling (hereinafter referred to as 2D-$IR_2$) is performed on the longitudinal magnetization of an upstream region 1402 of an artery on the left side by flip angle $\phi_2$ (for example, 90°). The regions on which the respective spatially-selective labeling is performed are approximately circular forms on the x-y plane, and are cylinder-shaped in the z-direction which are vertical to the imaging plane (on paper). Therefore, the blood flow portions to be actually labeled are the intersecting sections of the blood vessels and the cylinder-shaped regions. Accordingly, enhancement by the phase difference is performed on the blood flow portion of the artery on the right side, and enhancement by the signal intensity difference is performed on the blood flow portion of the artery on the left side. The order of labeling does not matter. Also, enhancement by the phase difference may be performed by applying 2D-$IR_1$ with respect to the blood flow portion of the artery on the left side, as well as performing enhancement by the signal intensity difference by applying 2D-$IR_2$ with respect to the blood flow portion of the artery on the right side.

As for the condition of standby time (TI), standby time (TI) of 2D-$IR_1$ for executing spatially-selective labeling by flip angle $\phi_1$ needs to be shorter than Limit TI, thus the limit of the equation (2) should be applied. On the other hand, the condition of an imaging region width ($FOV_b$) 1403 in the flow direction is determined by the following equation (10) by the standby time corresponding to the second spatially-selective labeling to be applied.

$$FOV_b < \text{Limit } FOV_b = \text{MIN}((TI_1 \text{ of } 2D\text{-}IR_1), (TI_2 \text{ of } 2D\text{-}IR_2)) \times Vba \quad (10)$$

Further, as shown in FIG. 14, it may also be configured so that an operator can input a target flow velocity of the labeling for each labeling portion on the positioning image, for optimizing an imaging region width ($FOV_b$) in the flow direction on the basis of the equations (8) and (9).

Next, the pulse sequence in the present embodiment will be described. The pulse sequence in the present embodiment is formed by a Main-Scan sequence and a Pre-Scan sequence as in the pulse sequence in the previously described Embodiment 1, and the detailed explanation of the Pre-Scan sequence will be omitted since it is the same as in Embodiment 1. The Main-Scan sequence in the present embodiment is formed, as in the previously described Embodiment 2, by an RF pre-pulse portion 1510 including two spatially-selective labeling portions (1501 and 1502) having different flip angles and standby times and the measurement sequence portion 551. The measurement sequence portion 551 is the same as the previously described Embodiments 1 and 2, thus the detailed description thereof is omitted, and the RF pre-pulse portion 1510 will be described in detail using the sequence chart shown in FIG. 15.

In the RF pre-pulse portion 1510, 2D-IR$_1$ (1501) is first executed for performing the spatially-selective labeling on the upstream region 1401 of the artery on the right side, and 2D-IR$_2$(1502) is executed next for performing spatially-selective labeling on the upstream region 1402 of the artery on the left side. RF, Gs, Gp and Gr in the respective spatially-selective labeling portions (1501 and 1502) have the waveform of the RF, Gz, Gx and Gy shown in FIG. 13 respectively, which is adjusted to the respectively corresponding excitation region and flip angle. Then the transverse magnetization generating RF pulse 504 of the measurement sequence portion 551 is applied in the timing at which the standby time from 2D-IR$_1$(1501) is TI$_1$ and the standby time from 2D-IR$_2$ (1502) is TI$_2$, and the measurement sequence portion 551 is started.

Further, as in the RF pre-pulse portion 1110 shown in FIG. 11 which is described in the previously described Embodiment 2, the spoiler gradient magnetic field pulses (1104-1~1104-3) are applied to the three axes after the execution of 2D-IR$_1$ (1501), the spoiler gradient magnetic field pulses (1107-1~1107-3) are applied to the three axes after the execution of 2D-IR$_2$ (1502), and each of the generated transverse magnetization is eliminated. In addition, the two spoiler gradient magnetic fields (1104 and 1107) can be put together and applied at one time for each axis also in the present embodiment.

Figure 16:
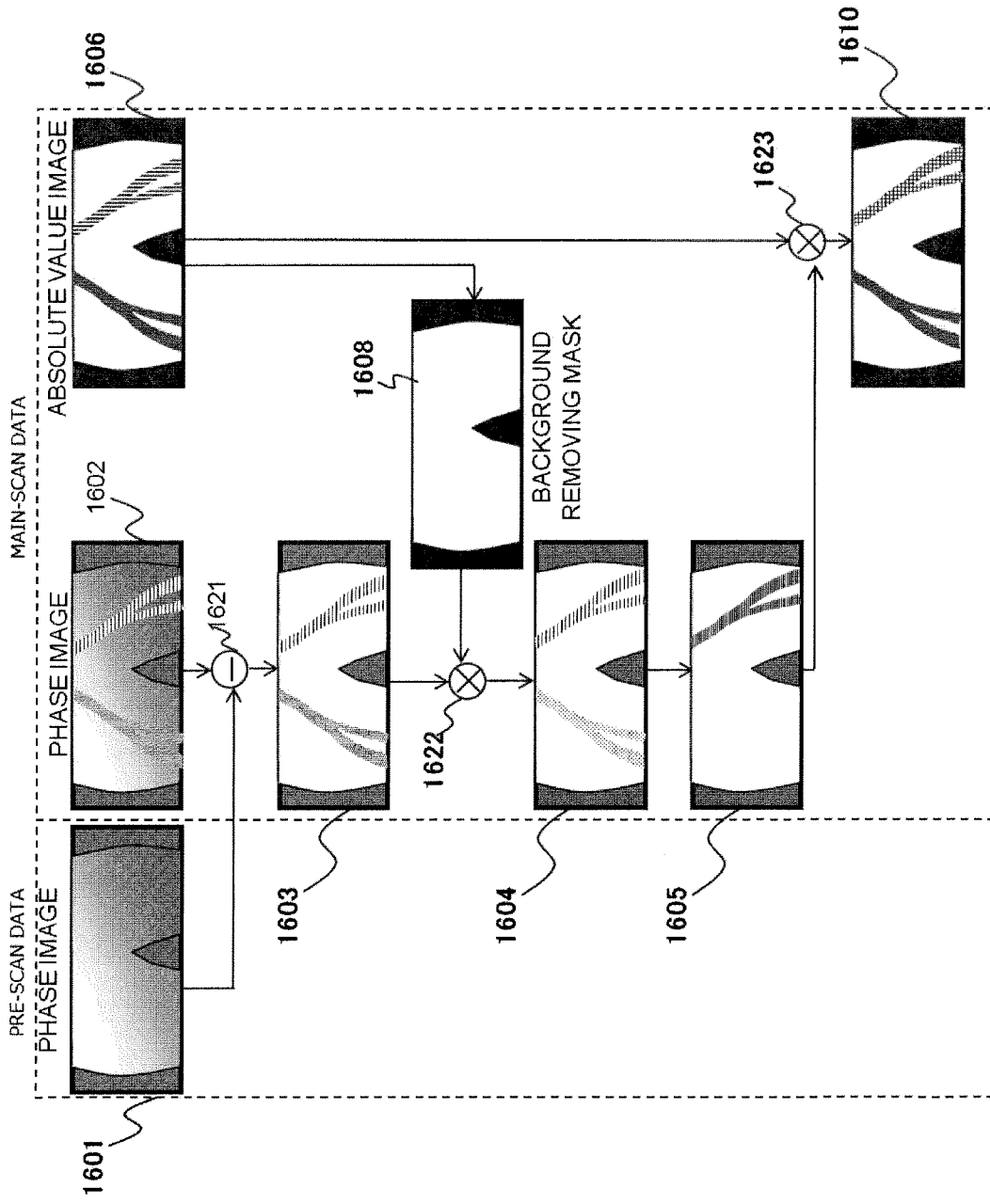
FIG. 16 is an example of the result obtained by executing the respective steps of the processing flow in Embodiment 3.

Next, the processing flow is the present embodiment will be described. The processing flow of the present embodiment is the same as the processing flow based on the flowchart shown in FIG. 7 described in Embodiment 1, but the processing content in a part of some of the steps is different, thus only the processing steps having different processing content will be described. Also, an example of the result obtained by executing the respective steps of the processing flow shown in FIG. 7 is shown in FIG. 16. The corresponding step numbers to FIG. 7 will be provided with "-3" in the following description.

In step 701-3, the sequence execution unit 601 displays the positioning image shown in FIG. 14, and receives the setting and input of the right-side labeling region 1401 and the left-side labeling region 1402 in the upstream side of an artery and the imaging region 1403. Then the sequence execution unit 601 checks whether or not an imaging can be performed referring to the other imaging conditions set and input by the operator. If the imaging is disapproved, the message thereof is notified to the operator, and receives the correction and input of the position or the width (diameter) of the right-side labeling region 1401, the left-side labeling region 1402 and the imaging region 1403 or the correction and input of the other imaging conditions acquired by presenting the operator of the possible imaging condition regarding the other imaging conditions. The final possible imaging condition is determined, and various control data necessary for performing the Main-Scan sequence shown in FIG. 15 and the Pre-Scan sequence shown in FIG. 5(b) is calculated in concrete terms on the basis of the determined imaging condition. Particularly, the respective RF, Gs, Gp and Gr are set so that each of the spatially-selective labeling portions (1501 and 1502) excites the right-side labeling region 1401 and the left-side labeling region 1402.

In step 702-3, the same processing as step 702 in Embodiment 1 is performed. As a result, a phase image (first phase image) 1601 of the low spatial resolution is obtained. The first phase image 1601 includes various errors other than the phase difference between the blood flow portion on the left side and the right side of the artery that are respectively labeled by the spatially-selective labeling portions (1501 and 1502) and the other stationary portion.

In step 703-3, the same processing as step 703 in Embodiment 1 is performed. As a result, the composite image and an absolute image 1606 are obtained, and a phase image (second phase image) 1602 is obtained from the composite image.

In step 704-3, the same processing as in step 704 in Embodiment 1 is performed. That, is, the phase difference image calculation unit 601 converts the first phase image 1601 obtained in step 702-3 into the phase image having the same spatial resolution as the second phase image 1602 obtained in step 703-3, and performs a difference processing 1621 between the converted first phase image and the second phase image 1602, thereby obtaining a phase difference image 1603. The phase difference image 1603 is the phase image from which the phase error due to the resonance frequency displacement and the phase error due to the incompleteness of the hardware are removed, and on which only the phase difference generated by short standby time (TI$_1$) after performing the spatially-selective labeling 1501 is reflected.

In step 705-3, the same processing as in step 705 in Embodiment 1 is performed. As a result, a first mask image 1608 is obtained.

In step 706-3, the same processing as in step 706 in Embodiment 1 is performed. That is, the mask processing unit 605 performs the first mask image 1608 created in step 705-3 on the phase difference image 1603 obtained in step 704-3 (1622), thereby obtaining a phase difference image 1604 in which the background region (noise region) is removed and only an object region is extracted from the phase difference image 1603.

In step 707-3, the same processing as in step 707 in Embodiment 1 is performed. As a result, in the corrected phase difference image, the phase of the blood flow portion of the left-side artery which is labeled in the stationary portion using 2D-IR$_2$ is zero, and the phase of the blood flow portion in the right-side artery which is labeled by 2D-IR$_1$ is π.

In step 708-3, the same processing as in step 708 of Embodiment 1 is performed.

In step 709-3, the same processing as step 709 in Embodiment 1 is performed. As a result, a second mask image 1605 is obtained. For example, it is possible to obtain the second mask image 1605 for weighting the intensity ratio of the right-side artery, the left-side artery and the stationary portion as 0.5:1:1 respectively.

In step 710-3, the same processing as step 710 in Embodiment 1 is performed. That is, the contrast enhancement processing unit 607 performs the second mask image 1605 obtained in step 709-3 on the absolute value image 1606 obtained in step 703-3 (1623). The weighting process (1623) using the second mask image 1605, i.e. based on the phase difference image 1603 is the contrast enhancement processing, and a contrast-enhanced image 1610 is obtained by this contrast enhancement processing.

The contrast-enhanced image 1610 is the image in which the labeled arteries on the left side and right side are suppressed with respect to the stationary portion. In concrete terms, the weighting is performed on the right-side artery portion with the intensity ratio of 0.5:1 between the artery portion and the stationary port n by the second mask image 1605 on the basis of the phase difference, and the weighting is performed on the left-side artery with the intensity ratio of 0:1 between the left-side artery and the stationary portion on the basis of the signal intensity difference in the absolute value image 1606. Then as a result of both weighting processing, the contrast-enhanced image 1610 is obtained in which the intensity ratio among the right-side artery portion, left-side artery portion and stationary portion is enhanced by 0.5:0:1 respectively. That is, not only the contrast between both of the labeled arteries and the other stationary portion, but also the contrast between the right and left arteries 801 is enhanced in the image.

In addition, since the absolute value image 1606 and the phase difference images (1603, 1604) correspond to the image in which the left-side artery is enhanced and the image in which the right-side artery is enhanced respectively which makes it easy to extract the respective regions, it is also possible to perform arbitrary coloring on the left and right arteries. With that, an image can be obtained in which the left and the right arteries are isolated from each other.

The processing flow in the present embodiment has been described above. While the case which enhances the phase difference of the right-side artery by performing the spatially-selective labeling 1501 and enhances the signal intensity difference of the left-side artery by performing the spatially-selective labeling 1502 has been described above, the phase-difference enhancement may also be performed on the left-side artery by performing spatially-selective labeling 1501 and the right-side artery may also be enhanced on the basis of the signal intensity difference by performing the spatially-selective labeling 1502 by the same processing. Also, the labeling by the 2-dimensional spatially-selective excitation may also be performed only on the left artery or the right artery, so as to obtain the contrast-enhanced image of only the enhanced artery.

As described above, the MRI apparatus and the fluid-enhanced image acquisition method in the present embodiment sets the RF pre-pulse as an RF pulse for executing 2-dimensional spatially-selective excitation, applies the RF pulse for executing 2-dimensional spatially-selective excitation on the region which intersects with at least a part of a fluid portion in the upstream side of an imaging region, and performs labeling on at least a part of the fluid portion. When the fluid portion has a first fluid portion (right-side artery) and a second fluid portion (left-side art and these portions are to be depicted by different contrast, the RF pre-pulse has a first RF pre-pulse (2D-IR$_1$) and a second RF pre-pulse (2D-IR$_2$) having different flip angles for executing 2-dimensional spatially-selective excitation, wherein the first RF pre-pulse is applied to the region which intersects with at least a part of the first fluid portion in the upstream side in an imaging region and the second RF pre-pulse is applied to the region which intersects with at least a part of the second fluid portion in the upstream side of the imaging region. In this manner, without increasing the imaging time, not only the left and the right arteries can be enhanced by different contrast with respect to the stationary portion, but also the left artery and the right artery can be enhanced by different contrast, thereby obtaining in a short period of time the image in which the left and the right arteries and the stationary portion can be distinguished clearly.

Embodiment 4

Next, Embodiment 4 of the MRI apparatus and the fluid-enhanced image acquisition method related to the present invention will be described. The RF pre-pulse portion in the present embodiment has two RF pre-pulses. The first RF pre-pulse is applied to a first region in the upstream side of a fluid portion, and a second RF pre-pulse is applied to a second region in the downstream side which is adjacent to the first region at the timing that the longitudinal magnetization which is flipped in a negative direction recovers by T1 to null. Then an imaging region is set in the second region. While the above-described respective embodiments measured the echo signal by setting the longitudinal magnetization in the blood flow portion in the negative condition state, the present embodiment measures the echo signal by setting in reverse the longitudinal magnetization of the stationary portion in the imaging region in a negative direction state. The present embodiment is especially effective in the case that the flow velocity is slow and a labeled fluid does not flow sufficiently into an imaging region.

Figure 17:
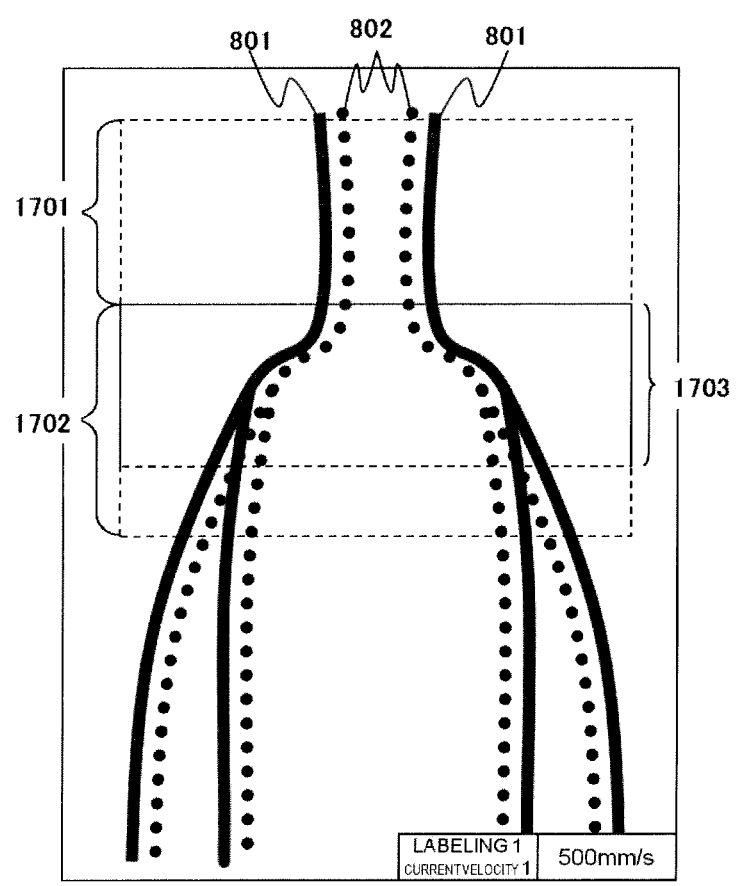
FIG. 17 is a setting example in Embodiment 4 of a labeling section by the respective IR pulses in a lower limb region.

The present embodiment will be described below in detail referring to FIGS. 17 and 18, using an RF pre-pulse as an IR pulse and exemplifying blood flow as a fluid portion. FIG. 17 is a setting example of labeling regions with respect to an artery (solid line) 801 and a vein (dotted line) 802 in a lower limb region. FIG. 18 shows the application timing of the respective IR pulses of the RF pre-pulse portion (RF) in the present embodiment and the behavior of the longitudinal magnetization of a fluid portion in the first region and a stationary portion in the second region in accordance with each of the timing.

First, the setting of the respective labeling regions will be described referring to FIG. 17. A first labeling region 1701 by an IR pulse 1801 is set in the upstream side for labeling the blood flow by the first flip angle $\phi_1$ (for example, 180°), and a second labeling region 1702 by an IR pulse 1802 is set in the downstream side which is adjacent to the first labeling region 1701 for labeling the blood flow by the next flip angle $\phi_2$ (for example, 180°). Then an imaging region (FOV) 1703 is set in the second labeling region 1702, and at least a part of the second labeling region 1702 is set as the imaging region 1703. FIG. 17 shows an example that the imaging region 1703 is set in the labeling region 1702. An operator sets the respective labeling regions and an imaging region on a positioning image. Further, an operator may also input a target flow velocity for the labeling for each labeling region on the positioning image, for optimizing the imaging region width (FOV$_b$) in the flow direction on the basis of the equations (8) and (9). After the imaging region width (FOVb) in the optimal flow direction is acquired and set, adjustment of the position and the width of the respective labeling regions is performed manually by the operator or automatically by the apparatus.

Next, the pulse sequence of the present embodiment will be described. The pulse sequence of the present embodiment, as in the pulse sequence in Embodiment 1, is formed by the Main-Scan sequence and the Pre-Scan sequence, and the Pre-Scan sequence is the same as Embodiment 1, thus the detailed description thereof will not be repeated. Also in the Main-Scan sequence, only the RF pre-pulse is different and the measurement sequence portion is the same as the previously described embodiment, thus only the RF pre-pulse portion will be described below in detail referring to FIG. 18. An RF pre-pulse portion 1810 in the present embodiment is formed having two IR pulses (1801 and 1802), wherein the first labeling region 1701 is excited by the first IR pulse 1801, then the second labeling region 1702 is excited by the second IR pulse 1802.

After application of the first IR pulse 1801 to the labeling region 1701, the second IR pulse 1802 is applied to the second labeling region 1702 after waiting for time TI$_1$ until the longitudinal magnetization of the blood flow reaches null. As a result, right after the application of the second IR pulse 1802, the longitudinal magnetization of the blood flow which is flown into the second labeling region and the imaging region 1703 stays in null condition, but the longitudinal magnetization of the other stationary portion in the second labeling region turns around 180 degrees to be in a negative direction state. By further waiting for time $TI_2$, the blood flow which is labeled in the first labeling region 1701 further flows into the imaging region 1703, and the longitudinal magnetization recovers by T1 to be in the positive direction state. In the meantime, waiting time ($TI_2$) is set as the time until the longitudinal magnetization of the other stationary portion in the second labeling region recovers by T1 to null and that a negative direction state of the longitudinal magnetization is maintained. Therefore, right before the transverse magnetization generating RF pulse 504 of the measurement sequence portion 551 is applied which is after the waiting time ($TI_2$) from the second IR pulse 1802 is applied, the longitudinal magnetization of the other stationary portion in the imaging region 1703 stays in the state of being recovered to a negative direction. When the echo signal is measured from the imaging 1703 by the measurement sequence portion 551 in the above-described state of longitudinal magnetization and an image is reconstructed from such measured echo signal, the phases of the longitudinal magnetizations in the blood flow portion and the other stationary portion can be differentiated by $\pi$. Further, any time length in which the longitudinal magnetization of the stationary portion in the imaging region 1703 maintains a negative direction can be used as waiting time ($TI_2$), thus greater flexibility can be provided for setting imaging parameters.

The processing after measuring the echo signal by the measurement sequence portion 551 is the same as the previously described Embodiment 1, thus the detailed explanation thereof will be omitted. In this regard, however, since the echo signal is measured in the present embodiment in the state that the longitudinal magnetization of the stationary portion in the imaging region is in a negative direction, the phase in the stationary portion in the phase difference image obtained in step 704 becomes $\pi$, but the corrected phase difference image in step 707 is corrected based on the phase in the stationary portion, thus the phase in the stationary portion becomes zero and the phase in the labeled blood flow portion becomes it ultimately in the corrected phase difference image as in the preciously described respective embodiments. For this reason, the processing after step 708 turns out to be the same.

As described above, in the MRI apparatus and the fluid-enhanced image acquisition method in the present embodiment, the RF pre-pulse portion includes a first RF pre-pulse (IR pulse 1801) and a second RF pre-pulse (IR pulse 1802), wherein the first RF pre-pulse is applied to a first region (first labeling region 1701) in the fluid portion for labeling a fluid portion, the second RF pre-pulse is applied to a second region (second labeling region 1702) which is adjacent to the downstream side of the first region, and at least a part of the second region is set as an imaging region. Then the second RF pre-pulse is applied at the timing that the Longitudinal magnetization in the fluid portion which is flipped in a negative direction by the first RF pre-pulse recovers by T1 to null, the echo signal from the imaging region is measured by the measurement sequence portion within the time that the longitudinal magnetization of the stationary portion in the second region which is flipped in a negative direction by the second RF pre-pulse maintains the negative direction state. In this manner, it is possible to obtain an image with enhanced contrast of the blood portion with respect to the other stationary portion without extending the imaging time, even when the flow velocity is slow.

The preferable embodiments of the present invention have been described above. However, the present invention is not limited to these embodiments.

While an example of extracting an phase error by pre-scan has been described in the respective embodiments above, highly-regulated MRI apparatuses may not have much phase error and pre-scan may not be needed, thus the present invention can be carried out with only main scan. In other words, in a highly-regulated MRI apparatus, a second mask image may be acquired based on the phase image obtained by performing the first mask image directly on the phase image obtained from main-scan data.

DESCRIPTION OF REFERENCE NUMERALS

101 object
102 static magnetic field generating magnet
103 gradient magnetic field coil
104 RF transmission coil
105 RF reception coil
106 signal detection unit
107 signal processing unit
108 overall control unit
109 gradient magnetic field source
110 RF transmission unit
111 measurement control unit
112 bed
113 display/operation unit
114 arithmetic processing unit
115 storage unit

The invention claimed is:

1. A magnetic resonance imaging apparatus comprising:
a measurement control unit configured to control measurement of an echo signal from an imaging region of an object to be examined including a fluid portion, on the basis of a predetermined pulse sequence; and
an arithmetic processing unit configured to obtain an image with enhanced contrast between the fluid portion and a stationary portion using the echo signal, wherein:
the pulse sequence is formed by an RF pre-pulse portion provided with an RF pre-pulse which performs labeling on the fluid portion by exciting the longitudinal magnetization of the fluid portion in a negative direction and a measurement sequence portion configured to measure an echo signal from the imaging region into which the labeled fluid portion is flown; and
the arithmetic processing unit obtains a fluid-enhanced image with enhanced contrast between the fluid portion and the stationary portion based on phase information of the image, and wherein
the measurement control unit performs labeling on the fluid portion by applying the RF pre-pulse to a region upstream from the imaging region, and executes the measurement sequence before the longitudinal magnetization of the labeled fluid portion is recovered to null or above, and wherein:
the RF pre-pulse includes an IR pulse which excites the longitudinal magnetization at $\alpha(90<\alpha<270)$-degrees; and
the measurement sequence portion includes a transverse magnetization generating RF pulse which generates transverse magnetization by exciting the longitudinal magnetization at $\beta(0<\beta\le90)$-degrees.

2. The magnetic resonance imaging apparatus according to claim 1, wherein the measurement control unit sets a waiting time (TI) between the IR pulse in the RF pre-pulse portion and the transverse magnetization generating RF pulse in the measurement sequence portion, as the time for maintaining the state that the longitudinal magnetization of the labeled fluid portion by the IR pulse is in a negative direction.

3. The magnetic resonance imaging apparatus according to claim 2, wherein the measurement control unit controls measurement of the echo signal by differentiating the phase of the transverse magnetization between the labeled fluid portion and the stationary portion by $\pi$, right after the application of the transverse magnetization generating RF pulse.

4. A magnetic resonance imaging apparatus comprising:
a measurement control unit configured to control measurement of an echo signal from an imaging region of an object to be examined including a fluid portion, on the basis of a predetermined pulse sequence; and
an arithmetic processing unit configured to obtain an image with enhanced contrast between the fluid portion and a stationary portion using the echo signal, wherein:
the pulse sequence is formed by an RF pre-pulse portion provided with an RF pre-pulse which performs labeling on the fluid portion by exciting the longitudinal magnetization of the fluid portion in a negative direction and a measurement sequence portion configured to measure an echo signal from the imaging region into which the labeled fluid portion is flown; and
the arithmetic processing unit obtains a fluid-enhanced image with enhanced contrast between the fluid portion and the stationary portion based on phase information of the image, and wherein
the arithmetic processing unit, on the basis of the phase image reconstructed using the echo signal measured by the measurement sequence portion, determines the weighting coefficient for each pixel in the image, thereby obtaining the fluid-enhanced image using the weighting coefficient.

5. The magnetic resonance imaging apparatus according to claim 4, wherein the arithmetic processing unit, on the basis of a phase difference image between the phase image which is reconstructed using the echo signal measured only by the measurement sequence portion and the phase image which is reconstructed using the echo signal measured in the RF pre-pulse portion and the measurement sequence portion, determines the weighting coefficient for each of the pixel, creates a mask image representing the distribution of the weighting coefficient, and multiplies the mask image by the absolute value image of the reconstructed image for each pixel, thereby obtaining the fluid-enhanced image.

6. The magnetic resonance imaging apparatus according to claim 5, wherein the arithmetic processing unit acquires the weighting coefficient in the phase difference image, by converting the phase of the fluid portion into the value of [0~1] and converting the phase of the other stationary portion into [1].

7. A magnetic resonance imaging apparatus comprising:
a measurement control unit configured to control measurement of an echo signal from an imaging region of an object to be examined including a fluid portion, on the basis of a predetermined pulse sequence; and
an arithmetic processing unit configured to obtain an image with enhanced contrast between the fluid portion and a stationary portion using the echo signal, wherein:
the pulse sequence is formed by an RF pre-pulse portion provided with an RF pre-pulse which performs labeling on the fluid portion by exciting the longitudinal magnetization of the fluid portion in a negative direction and a measurement sequence portion configured to measure an echo signal from the imaging region into which the labeled fluid portion is flown; and
the arithmetic processing unit obtains a fluid-enhanced image with enhanced contrast between the fluid portion and the stationary portion based on phase information of the image, and wherein
the measurement control unit performs labeling on the fluid portion by applying the RF pre-pulse to a region upstream from the imaging region, and executes the measurement sequence before the longitudinal magnetization of the labeled fluid portion is recovered to null or above, and wherein:
the fluid portion has a first fluid portion and a second fluid portion having different flow directions;
the RF pre-pulse portion includes a first RF pre-pulse and a second RF pre-pulse having different flip angles;
the measurement control unit performs labeling on the first fluid portion by applying the first RF pre-pulse on a first region upstream of the first fluid portion, performs labeling on the second fluid portion by applying the second pre-pulse to a second region upstream of the second fluid portion, and sets the region between the first region and the second region as the imaging region; and
the arithmetic processing unit obtains the fluid-enhanced image by differentiating the contrast between the first fluid portion and the second fluid portion.

8. The magnetic resonance imaging apparatus according to claim 7, wherein:
the first RF pre-pulse is an IR pulse with flip angle of $\phi_1(90<\phi_1<270)$-degrees;
the second RF pre-pulse is an IR pulse with flip angle $\phi_2(0<\phi_2\leq90)$-degrees;
the measurement control unit executes the measurement sequence portion before the longitudinal magnetization of the first fluid portion recovers to null or above; and
the arithmetic processing unit enhances the contrast of the first fluid portion on the basis of the phase information, and enhances the contrast of the second fluid portion on the basis of the signal intensity difference between the fluid portion and the stationary portion.

9. A magnetic resonance imaging apparatus comprising:
a measurement control unit configured to control measurement of an echo signal from an imaging region of an object to be examined including a fluid portion, on the basis of a predetermined pulse sequence; and
an arithmetic processing unit configured to obtain an image with enhanced contrast between the fluid portion and a stationary portion using the echo signal, wherein:
the pulse sequence is formed by an RF pre-pulse portion provided with an RF pre-pulse which performs labeling on the fluid portion by exciting the longitudinal magnetization of the fluid portion in a negative direction and a measurement sequence portion configured to measure an echo signal from the imaging region into which the labeled fluid portion is flown; and
the arithmetic processing unit obtains a fluid-enhanced image with enhanced contrast between the fluid portion and the stationary portion based on phase information of the image, and wherein
the measurement control unit performs labeling on the fluid portion by applying the RF pre-pulse to a region upstream from the imaging region, and executes the measurement sequence before the longitudinal magnetization of the labeled fluid portion is recovered to null or above, and wherein:

the RF pre-pulse is for executing 2-dimensional spatially-selective excitation; and the measurement control unit applies the RF pulse for executing 2-dimensional spatially-selective excitation on the region which intersects with at least a part of a fluid region upstream of the imaging region, for labeling at least a part of the fluid portion.

10. The magnetic resonance imaging apparatus according to claim 9, wherein:

the fluid portion has a first fluid portion and a second fluid portion;

the RF pre-pulse includes a first RF pre-pulse and a second RF pre-pulse having different flip angles for executing the 2-dimensional spatially-selective excitation; and the measurement control unit applies the first RF pre-pulse to a region which intersects with at least a part of the first fluid portion upstream of the imaging region, and applies the second RF pre-pulse to a region which intersects with at least a part of the second fluid portion upstream of the imaging region.

11. A magnetic resonance imaging apparatus comprising:

a measurement control unit configured to control measurement of an echo signal from an imaging region of an object to be examined including a fluid portion, on the basis of a predetermined pulse sequence; and an arithmetic processing unit configured to obtain an image with enhanced contrast between the fluid portion and a stationary portion using the echo signal, wherein:

the pulse sequence is formed by an RF pre-pulse portion provided with an RF pre-pulse which performs labeling on the fluid portion by exciting the longitudinal magnetization of the fluid portion in a negative direction and a measurement sequence portion configured to measure an echo signal from the imaging region into which the labeled fluid portion is flown; and the arithmetic processing unit obtains a fluid-enhanced image with enhanced contrast between the fluid portion and the stationary portion based on phase information of the image, and wherein the measurement control unit performs labeling on the fluid portion by applying the RF pre-pulse to a region upstream from the imaging region, and executes the measurement sequence before the longitudinal magnetization of the labeled fluid portion is recovered to null or above, and wherein:

the RF pre-pulse portion has a first RF pre-pulse and a second RF pre-pulse; and the measurement control unit performs labeling on the fluid portion by applying the first RF pre-pulse to a first region upstream of the fluid portion, applies the second RF pre-pulse to a second region which is adjacent to downstream of the first region, and sets at least a part of the second region as the imaging region.

12. The magnetic resonance imaging apparatus according to claim 11, wherein the measurement control unit applies the second RF pre-pulse at the timing that the longitudinal magnetization of the fluid portion flipped in a negative direction by the first RF pre-pulse recovers by T1 to null, and controls measurement of the echo signal from the imaging region by the measurement sequence portion within the time that the longitudinal magnetization of the stationary portion in the second region flipped in a negative direction by the second RF pre-pulse maintains the negative direction state.

13. A fluid-enhanced image acquisition method including:

a measurement step of controlling measurement of an echo signal from an imaging region of an object to be examined including a fluid portion, on the basis of a predetermined pulse sequence; and an arithmetic processing step of obtaining an image with enhanced contrast between the fluid portion and a stationary portion using the echo signal, wherein:

the pulse sequence has an RF pre-pulse portion comprising an RF pre-pulse for labeling the fluid portion by exciting the longitudinal magnetization of the fluid portion in a negative direction and a measurement sequence portion which measures an echo signal from the imaging region into which the labeled fluid portion is flown; and the arithmetic processing step obtains an image with enhanced contrast between the fluid portion and the stationary portion based on phase information of the image, and wherein the measurement step applies the RF pre-pulse to a region upstream from the imaging region, and executes the measurement sequence portion before the longitudinal magnetization of the fluid portion recovers to null, and wherein:

the fluid portion includes a first fluid portion and a second fluid portion having different directions;

the RF pre-pulse portion has a first RF pre-pulse and a second RF pre-pulse having different flip angles;

the measurement step performs labeling on the first fluid portion by applying the first RF pre-pulse on a first region upstream of the first fluid portion, performs labeling on the second fluid portion by applying the second RF pre-pulse on a second region upstream of the second fluid portion, and sets a region between the first region and the second region as the imaging region; and the arithmetic processing step obtains the fluid-enhanced image by differentiating the contrast between the first fluid portion and the second fluid portion.

14. A fluid-enhanced image acquisition method including:

a measurement step of controlling measurement of an echo signal from an imaging region of an object to be examined including a fluid portion, on the basis of a predetermined pulse sequence; and an arithmetic processing step of obtaining an image with enhanced contrast between the fluid portion and a stationary portion using the echo signal, wherein:

the pulse sequence has an RF pre-pulse portion comprising an RF pre-pulse for labeling the fluid portion by exciting the longitudinal magnetization of the fluid portion in a negative direction and a measurement sequence portion which measures an echo signal from the imaging region into which the labeled fluid portion is flown; and the arithmetic processing step obtains an image with enhanced contrast between the fluid portion and the stationary portion based on phase information of the image, and wherein the measurement step applies the RF pre-pulse to a region upstream from the imaging region, and executes the measurement sequence portion before the longitudinal magnetization of the fluid portion recovers to null, and wherein:

the RF pre-pulse is an RF pulse for executing 2-dimensional spatially-selective excitation; and the measurement step applies the RF pulse for executing 2-dimensional spatially-selective excitation to a region which intersects with at least a part of the fluid portion upstream of the imaging region, for labeling at least a part of the fluid portion.

15. A fluid-enhanced image acquisition method including:
a measurement step of controlling measurement of an echo signal from an imaging region of an object to be examined including a fluid portion, on the basis of a predetermined pulse sequence; and
an arithmetic processing step of obtaining an image with enhanced contrast between the fluid portion and a stationary portion using the echo signal, wherein:
the pulse sequence has an RF pre-pulse portion comprising an RF pre-pulse for labeling the fluid portion by exciting the longitudinal magnetization of the fluid portion in a negative direction and a measurement sequence portion which measures an echo signal from the imaging region into which the labeled fluid portion is flown; and
the arithmetic processing step obtains an image with enhanced contrast between the fluid portion and the stationary portion based on phase information of the image, wherein:
the RF pre-pulse portion has a first RF pre-pulse and a second RF pre-pulse; and
the measurement step labels the fluid portion by applying the first RF pre-pulse on a first region upstream of the fluid portion, applies the second RF pre-pulse to a second region adjacent to the side downstream of the first region, and sets at least a part of the second region as the imaging region.

* * * * *